United States Patent
Safouane et al.

(10) Patent No.: US 11,679,069 B2
(45) Date of Patent: Jun. 20, 2023

(54) COSMETIC OR DERMATOLOGICAL COMPOSITION COMPRISING A MEROCYANINE AND AN OILY PHASE COMPRISING AT LEAST ONE ALKYL OR ALKYLENE CARBONATE

(71) Applicant: L'OREAL, Paris (FR)

(72) Inventors: Mahassine Safouane, Chevilly la Rue (FR); Amélie Baron, Chevilly la Rue (FR); Julie Grumelard, Village-Neuf (FR)

(73) Assignee: L'OREAL, Paris (FR)

(*) Notice: Subject to any disclaimer, the term of this patent is extended or adjusted under 35 U.S.C. 154(b) by 74 days.

(21) Appl. No.: 16/973,141

(22) PCT Filed: Jun. 27, 2019

(86) PCT No.: PCT/EP2019/067228
§ 371 (c)(1),
(2) Date: Dec. 8, 2020

(87) PCT Pub. No.: WO2020/002537
PCT Pub. Date: Jan. 2, 2020

(65) Prior Publication Data
US 2021/0251868 A1  Aug. 19, 2021

(30) Foreign Application Priority Data
Jun. 28, 2018 (FR) ....................... 1855828

(51) Int. Cl.
| A61K 8/44 | (2006.01) |
|---|---|
| A61K 8/49 | (2006.01) |
| A61Q 1/02 | (2006.01) |
| A61Q 17/04 | (2006.01) |
| A61Q 19/00 | (2006.01) |
| A61Q 19/08 | (2006.01) |

(52) U.S. Cl.
CPC .......... *A61K 8/44* (2013.01); *A61K 8/49* (2013.01); *A61K 8/4926* (2013.01); *A61K 8/4973* (2013.01); *A61Q 1/02* (2013.01); *A61Q 17/04* (2013.01); *A61Q 19/00* (2013.01); *A61Q 19/08* (2013.01)

(58) Field of Classification Search
None
See application file for complete search history.

(56) References Cited

FOREIGN PATENT DOCUMENTS

| JP | 2014-529337 A | 11/2014 |
|---|---|---|
| JP | 2014-533708 A | 12/2014 |
| JP | 2016-540005 A | 12/2016 |
| WO | WO 2013/011094 A2 | 1/2013 |
| WO | WO 2013/076075 A2 | 5/2013 |
| WO | WO 2014/111568 A1 | 7/2014 |
| WO | WO 2015/094760 A1 | 6/2015 |
| WO | WO 2017/042227 A2 | 3/2017 |

OTHER PUBLICATIONS

Cao et al. "Enhancing Sun Care Using Bentone Hectorite Clay Technology". Cosmetic Science Technology (Year: 2006).*
Elementis. Safety Data Sheet. "Bentone Gel IPM V". <https://www.elementis.com/sds> (Year: 2018).*
Anonymous: "Merocyanine derivatives for cosmetic use", ip.com Journal, Mar. 4, 2004, XP013014587.
Anonymous: "Use of merocyanine derivatives as UV absorbers in cosmetic formulations (I)", ip.com Journal, Feb. 23, 2009, XP013129682.

* cited by examiner

*Primary Examiner* — Nicole P Babson
(74) *Attorney, Agent, or Firm* — Polsinelli PC

(57) ABSTRACT

A cosmetic or dermatological composition comprising:
a) at least one merocyanine of formula (1) or (2)

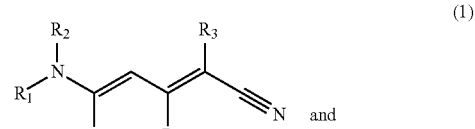

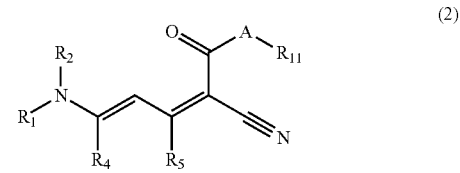

b) at least one oily phase comprising at least one alkyl or alkylene carbonate is provided. Also provided is a non-therapeutic cosmetic process for caring for and/or making up a keratin material, comprising applying to the surface of the keratin material, of at least one of the above compositions. Also provided is a non-therapeutic cosmetic process for limiting the darkening of the skin and/or improving the colour and/or uniformity of the complexion, comprising applying to the surface of the keratin material, of at least one of the above compositions. In addition, provided is a non-therapeutic cosmetic process for preventing and/or treating the signs of ageing of a keratin material, comprising applying to the surface of the keratin material, of at least one of the above compositions.

32 Claims, No Drawings

COSMETIC OR DERMATOLOGICAL COMPOSITION COMPRISING A MEROCYANINE AND AN OILY PHASE COMPRISING AT LEAST ONE ALKYL OR ALKYLENE CARBONATE

CROSS REFERENCE TO RELATED APPLICATIONS

This application is a National Phase filing under 35 U.S.C. § 371 of PCT/EP2019/067228 filed on 27 Jun. 2019; which application in turn claims priority to Application No. 1855828 filed in France on 28 Jun. 2018. The entire contents of each application are hereby incorporated by reference.

The present invention relates to a cosmetic or dermatological composition comprising:
a) at least one merocyanine of formula (1) or (2) that will be defined below in detail and
b) at least one oily phase comprising at least one alkyl or alkylene carbonate.

The present invention also relates to a non-therapeutic cosmetic process for caring for and/or making up a keratin material, comprising the application, to the surface of said keratin material, of at least one composition according to the invention as defined above.

The invention also relates to a non-therapeutic cosmetic process for limiting the darkening of the skin and/or improving the colour and/or uniformity of the complexion, comprising the application, to the surface of the keratin material, of at least one composition as defined previously.

The invention also relates to a non-therapeutic cosmetic process for preventing and/or treating the signs of ageing of a keratin material, comprising the application, to the surface of the keratin material, of at least one composition as defined previously.

It is known that radiation with wavelengths of between 280 nm and 400 nm allows tanning of the human epidermis and that radiation with wavelengths of between 280 and 320 nm, known under the name UVB rays, harms the development of a natural tan. Exposure is also liable to induce impairment of the biomechanical properties of the epidermis, which is reflected by the appearance of wrinkles, leading to premature ageing of the skin.

It is also known that UVA rays with wavelengths of between 320 and 400 nm penetrate more deeply into the skin than UVB rays. UVA rays cause immediate and persistent browning of the skin. Under normal conditions, daily exposure to UVA rays, even of short duration, can result in damage to the collagen fibres and the elastin, which is reflected by a modification to the microrelief of the skin, the appearance of wrinkles and uneven pigmentation (liver spots, non-uniformity of the complexion).

Protection against UVA and UVB radiation is therefore necessary. An effective photoprotective product must protect against both UVA and UVB radiation.

Many photoprotective compositions have been proposed to date to overcome the effects induced by UVA and/or UVB radiation. They generally contain organic UV screening agents and/or inorganic UV screening agents, which function according to their own chemical nature and according to their own properties by absorption, reflection or scattering of the UV radiation. They generally contain mixtures of liposoluble organic screening agents and/or of water-soluble UV-screening agents combined with metal oxide pigments such as titanium dioxide or zinc oxide.

Many cosmetic compositions intended to limit darkening of the skin, and to improve the colour and uniformity of the complexion have been proposed to date. It is well known in the field of antisun products that such compositions can be obtained by using UV-screening agents, and in particular UVB-screening agents. Some compositions may also contain UVA-screening agents. This screening system must cover UVB protection for the purpose of limiting and controlling the neosynthesis of melanin promoting overall pigmentation, but must also cover UVA protection in order to limit and control the oxidation of the already existing melanin resulting in darkening of the skin.

However, it is extremely difficult to find a composition containing a particular combination of UV-screening agents that would be specially suitable for photoprotection of the skin and particularly for an improvement in the quality of the skin both in terms of the colour and in terms of its mechanical elasticity properties.

Advantageously, this improvement is particularly desired on skin that is already pigmented, for the purpose of not increasing either the pigmentary melanin load or the structure of the melanin already present within the skin.

In fact, the majority of organic UV-screening agents consist of aromatic compounds which absorb in the wavelength range between 280 and 370 nm. In addition to their solar radiation-screening capacity, the desired photoprotective compounds must also have good cosmetic properties, good solubility in the usual solvents and in particular in fatty substances such as oils, and also good photostability alone or in combination with other UV-screening agents. They must also be colourless or at least have a colour that is cosmetically acceptable for consumers.

One of the main drawbacks known to date of these compositions is that these screening systems have insufficient efficiency against UV radiation and particularly against long UVA radiation with wavelengths above 370 nm with the aim of controlling light-induced pigmentation and the evolution thereof by means of a system which screens out UV radiation over the whole of the UV spectrum.

Among all the compounds that have been recommended for this purpose, an advantageous family of UV-screening agents which consists of carbonated merocyanine derivatives has been proposed, which is described in patent U.S. Pat. No. 4,195,999, patent application WO 2004/006878 and document IP COM Journal 4 (4), 16 No. IPCOM000011179D published on Apr. 3, 2004. These compounds have very good screening properties in the long UVA radiation range, but have poorly satisfactory solubility in the usual solvents and in particular in fatty substances such as oils, and an unsatisfactory photostability for some merocyanines.

With the aim of searching for other merocyanines which have better solubility in the usual solvents and better photostability, patent application WO2013/011094 proposed merocyanines comprising polar groups consisting of hydroxyl and ether functions, which show good long UVA-screening efficiency. However, the oil-solubility of these particular merocyanines is still not entirely satisfactory, and often requires a fastidious formulating process. Moreover, the large amounts of solvent that are required to dissolve this type of merocyanine may lead to cosmetic drawbacks such as a tacky and greasy effect on application.

The need thus remains to improve the solubility of these merocyanines in photoprotective formulations comprising at least one oily phase, in particular over time.

The Applicant has discovered, surprisingly, that by using alkyl or alkylene carbonates, it is possible to substantially improve the solubility of these merocyanines in an oily phase over time and at a low temperature. This discovery forms the basis of the present invention.

Thus, in accordance with one of the subjects of the present invention, a notably cosmetic or dermatological composition is now proposed, which comprises: a) at least one merocyanine of formula (1) or (2) which will be defined in detail later and b) at least one oily phase and comprising at least one alkyl or alkylene carbonate.

The present invention also relates to a non-therapeutic cosmetic process for caring for and/or making up a keratin material, comprising the application, to the surface of said keratin material, of at least one composition according to the invention as defined above.

The invention also relates to a non-therapeutic cosmetic process for limiting the darkening of the skin and/or improving the colour and/or uniformity of the complexion, comprising the application, to the surface of the keratin material, of at least one composition as defined previously.

The invention also relates to a non-therapeutic cosmetic process for preventing and/or treating the signs of ageing of a keratin material, comprising the application, to the surface of the keratin material, of at least one composition as defined previously.

Other characteristics, aspects and advantages of the invention will become apparent on reading the detailed description which follows.

The term "keratin materials" means the skin (of the body, face and around the eyes), the hair, eyelashes, eyebrows, body hair, nails, lips or mucous membranes.

The term "physiologically acceptable" means compatible with the skin and/or its integuments, which has a pleasant colour, odour and feel, and which does not cause any unacceptable discomfort (stinging, tautness or redness) liable to discourage the consumer from using this composition.

The term "between X and Y" means the range of values also including the limits X and Y.

According to the invention, the term "preventing" or "prevention" means reducing the risk of occurrence or slowing down the occurrence of a given phenomenon, namely, according to the present invention, the signs of ageing of a keratin material.

Merocyanines

According to the present invention, the merocyanine compounds in accordance with the invention correspond to formula (1) or (2) below

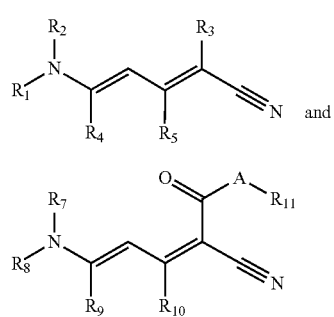

in which:

$R_1$ and $R_2$, independently of each other, are hydrogen; a $C_1$-$C_{22}$ alkyl group, a $C_2$-$C_{22}$ alkenyl group, or a $C_2$-$C_{22}$ alkynyl group, these groups possibly being substituted with at least one hydroxyl group or else interrupted with at least one —O—; or else $R_1$ and $R_2$ form, together with the nitrogen atom which links them, a —$(CH_2)_n$— ring which may be optionally interrupted with —O— or —NH—;

$R_3$ is a —(C=O)O$R_6$ group; or a —(CO)NH$R_6$ group;

$R_6$ is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, said groups possibly being substituted with one or more OH;

$R_4$ and $R_5$ are hydrogens; or $R_4$ and $R_5$ form a —$(CH_2)_n$— ring which may be substituted with a $C_1$-$C_4$ alkyl group and/or interrupted with one or more —O— or with —NH—;

n is a number between 2 and 7;

$R_7$ and $R_8$, independently of each other, are hydrogen; a $C_1$-$C_{22}$ alkyl group, a $C_2$-$C_{22}$ alkenyl group, a $C_2$-$C_{22}$ alkynyl group, said groups possibly being interrupted with one or more O and/or substituted with one or more OH; a $C_3$-$C_{22}$ cycloalkyl group or a $C_3$-$C_{22}$ cycloalkenyl group, said groups possibly being interrupted with one or more —O—;

or else $R_7$ and $R_8$ form, together with the nitrogen which links them, a —$(CH_2)_n$— ring which may be interrupted with one or more —O—;

$R_9$ and $R_{10}$ are hydrogen; or $R_9$ and $R_{10}$ form a —$(CH_2)_n$— ring potentially substituted with a $C_1$-$C_4$ alkyl and/or interrupted with an —O— or —NH—;

n is a number between 2 and 7

A is —O—; or —NH;

$R_{11}$ is a $C_1$-$C_{22}$ alkyl group; a $C_2$-$C_{22}$ alkenyl group; a $C_2$-$C_{22}$ alkynyl group; a $C_3$-$C_{22}$ cycloalkyl group or a $C_3$-$C_{22}$ cycloalkenyl group, said groups possibly being interrupted with one or more O; or a $C_1$-$C_{22}$ alkyl group or a $C_2$-$C_{22}$ alkenyl group which is substituted with a $C_3$-$C_{22}$ cycloalkyl group or a $C_3$-$C_{22}$ cycloalkenyl group, said $C_3$-$C_{22}$ cycloalkyl group or $C_3$-$C_{22}$ cycloalkenyl group possibly being interrupted with one or more —O—;

Preferably, the compounds of formulae (1) or (2) have the following characteristics:

(I) at least one of the $R_1$, $R_2$ or $R_6$ groups is substituted with a hydroxyl;

(II) if one of the $R_1$ denotes a hydroxyethyl, $R_2$ does not denote a hydrogen, a methyl or an ethyl or a hydroxyethyl; and if $R_1$ denotes hydrogen, $R_2$ is not 1-hydroxy-3-methyl but-2-yl;

(III) if $R_6$ is substituted with one or more OH, one of $R_1$ or $R_2$ is a $C_4$-$C_{22}$ alkyl group; or else $R_1$ and $R_2$ form, together with the nitrogen to which they are bonded, a piperidyl or morpholinyl radical;

(IV) at least one from among the radicals $R_7$, $R_8$ and $R_{11}$ is interrupted with one or more —O—.

The preferred compounds are those of formula (1) or (2) in which:

$R_1$ and $R_2$, independently of each other, are hydrogen; a $C_4$-$C_{12}$ alkyl group; or a $C_3$-$C_{12}$ hydroxyalkyl group; or at least one of $R_1$ or $R_2$ is a $C_3$-$C_{12}$ hydroxyalkyl group and $R_3$, $R_4$ and $R_5$ have the same meanings indicated previously.

The preferred compounds are also those of formula (1) in which:

$R_6$ is a $C_1$-$C_{12}$ alkyl group, which may be substituted with one or more hydroxyls.

The compounds which are the most preferential are also those of formula (1), in which:

$R_6$ is a $C_1$-$C_{12}$ alkyl group, which may be substituted with one or more hydroxyls; one of the $R_1$ or $R_2$ radicals is a $C_4$-$C_{22}$ alkyl group; or else $R_1$ and $R_2$ form, together with the nitrogen which links them, a —(CH$_2$)$_n$— ring which may be interrupted with —O— and/or —NH—; and R$_4$ and R$_5$ and n have the same meanings indicated previously.

The preferred compounds are those of formula (2) in which:

R$_{11}$ is a —(CH$_2$)$_m$—O—R$_{12}$ radical, in which

R$_{12}$ is a C$_1$-C$_{12}$ alkyl group; or a C$_1$-C$_6$ alkoxy-C$_1$-C$_6$ alkyl group;

m is a number from 1 to 5; and

R$_7$, R$_8$, R$_9$, R$_{10}$ and A have the same meanings indicated previously.

The compounds that are even more preferential are those of formula (1) or (2), in which:

R$_1$ and R$_2$, on the one hand, and R$_7$ and R$_8$, on the other hand, respectively form, together with the nitrogen atom to which they are respectively bonded, a piperidyl radical or a morpholinyl radical.

The preferred compounds are also those of formulae (1) and (2), in which: R$_4$ and R$_5$ and R$_9$ and R$_{10}$ respectively form a carbon-based ring which contains 6 carbon atoms.

The most preferential compounds are those of formula (1), in which:

R$_1$ and R$_2$, independently of each other, are a hydrogen; or a C$_1$-C$_{22}$ alkyl group; or a C$_1$-C$_{22}$ hydroxyalkyl group; or R$_1$ and R$_2$ form, together with the nitrogen atom to which they are bonded, a piperidyl or morpholinyl radical;

R$_3$ is a —(C=O)OR$_6$ group; or a —(CO)NHR$_6$ group;

R$_6$ is a C$_1$-C$_{22}$ alkyl group, which may be substituted with one or more —OH;

R$_4$ and R$_5$ are hydrogen; or R$_4$ and R$_5$ are linked together to form a carbon-based ring which contains 6 carbon atoms.

The most preferential compounds are those of formula (1), in which:

R$_1$ and R$_2$, independently of each other, are a hydrogen; or a C$_1$-C$_{22}$ hydroxyalkyl group; in which at least one of the R$_1$ and R$_2$ radicals is a C$_1$-C$_{22}$ hydroxyalkyl group;

R$_3$ is a —(C=O)OR$_6$ group; or a —(C=O)NHR$_6$ group;

R$_6$ is a C$_1$-C$_{22}$ alkyl group; and

R$_4$ and R$_5$ are hydrogens; or R$_4$ and R$_5$ are bonded together to form a carbon-based ring which contains 6 carbon atoms.

The most preferential compounds are those of formula (2), in which:

R$_7$ and R$_8$, independently of each other, are a hydrogen or a C$_1$-C$_8$ alkyl group, which may be with one or more —O—;

A is —O— or —NH;

R$_{11}$ is a C$_1$-C$_{22}$ alkyl; and

R$_9$ and R$_{10}$ are a hydrogen; or R$_9$ and R$_{10}$ are bonded together to form a carbon-based ring which contains 6 carbon atoms.

The most preferential compounds are those of formula (2), in which:

R$_7$ and R$_8$ form, together with the nitrogen atom to which they are bonded, a morpholinyl or piperidyl radical;

A is —O— or —NH;

R$_{11}$ is a C$_1$-C$_{22}$ alkyl group, which may be interrupted with one or more —O—; and R$_9$ and R$_{10}$ are hydrogens; or R$_9$ and R$_{10}$ are bonded together to form a carbon-based ring which contains 6 carbon atoms.

The compounds that are even more preferential are those of formula (2), in which:

R$_{11}$ is a —(CH$_2$)$_m$—O—R$_{12}$ radical, in which

R$_{12}$ is a C$_1$-C$_4$ alkyl group; or a C$_1$-C$_4$ alkoxy-C$_1$-C$_4$ alkyl group;

m is a number from 1 to 3; and

R$_7$ and R$_8$, independently of each other, are a hydrogen; a C$_1$-C$_{12}$ alkyl group, which may be interrupted with one or more O; or R$_7$ and R$_8$ form, together with the nitrogen atom to which they are bonded, a morpholinyl or piperidyl radical;

R$_9$ and R$_{10}$ are hydrogens or together form a carbon-based ring which contains 6 carbon atoms; and A is —O— or —NH.

The merocyanine compounds of the invention may be in the E/E-, E/Z- or Z/Z geometrical isomer form.

The alkyl, cycloalkyl, alkenyl, alkylidene or cycloalkenyl chains may be linear or branched, monocyclic or polycyclic chains.

A C$_1$-C$_{22}$ alkyl group is, for example, a methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

A substituted alkyl group is, for example, a methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-[2,4-bis(tert-amyl)phenoxy]propyl, ethoxycarbonylmethyl-2-(2-hydroxyethoxy)ethyl or 2-furylethyl.

A hydroxy-substituted alkyl group is, for example, a hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl.

A C$_2$-C$_{22}$ alkenyl group is, for example, a linear C$_2$-C$_{12}$ alkenyl chain or preferentially a branched C$_3$-C$_{12}$ alkenyl chain. A C$_2$-C$_{22}$ alkenyl is, for example, a vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the various isomers of hexenyl, octenyl, noenyl, decenyl or dodecenyl.

A C$_3$-C$_{12}$ cycloalkyl group is, for example, a cyclopropyl, cyclobutyl, cyclopentyl or trimethylcyclohexyl or, preferentially, a cyclohexyl.

Examples of merocyanines according to the present invention are listed in Table A:

TABLE A

| Compound | Structure |
|---|---|
| 1 | 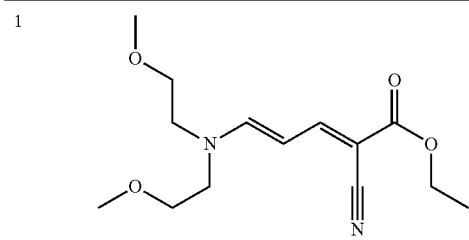 |

TABLE A-continued

| Compound | Structure |
|---|---|
| 2 | 2-methoxyethyl 2-cyano-5-[bis(2-methoxyethyl)amino]penta-2,4-dienoate |
| 3 | 2-ethoxyethyl 2-cyano-5-[bis(2-methoxyethyl)amino]penta-2,4-dienoate |
| 4 | 2-ethoxyethyl 2-cyano-5-(piperidin-1-yl)penta-2,4-dienoate |
| 5 | 2-(2-methoxyethoxy)ethyl 2-cyano-5-(piperidin-1-yl)penta-2,4-dienoate |
| 6 | 2-cyano-N-(2-hydroxyethyl)-5-(piperidin-1-yl)penta-2,4-dienamide |
| 7 | 2,3-dihydroxypropyl 2-cyano-5-(piperidin-1-yl)penta-2,4-dienoate |
| 8 | 2-hydroxypentyl 2-cyano-5-(piperidin-1-yl)penta-2,4-dienoate |
| 9 | 2,3-dihydroxypropyl 2-cyano-5-(morpholin-4-yl)penta-2,4-dienoate |

TABLE A-continued
| Compound | Structure |
|---|---|
| 10 | 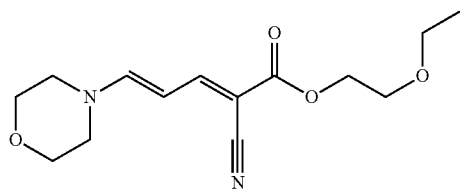 [SMILES: CCOCCOC(=O)/C(C#N)=C/C=C/N1CCOCC1] |
| 11 | 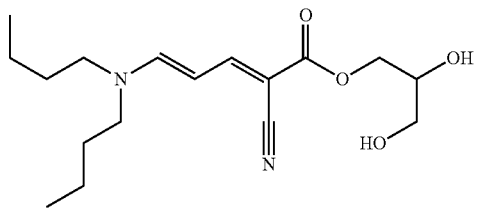 [SMILES: CCCCN(/C=C/C=C(\C#N)C(=O)OCC(O)CO)CCCC] |
| 12 | 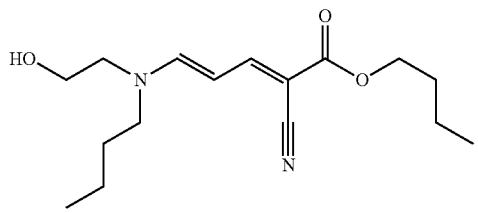 [SMILES: CCCCOC(=O)/C(C#N)=C/C=C/N(CCO)CCCC] |
| 13 | 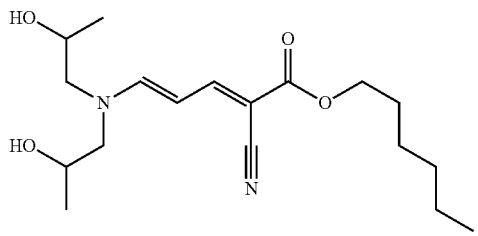 [SMILES: CCCCCCOC(=O)/C(C#N)=C/C=C/N(CC(C)O)CC(C)O] |
| 14 | 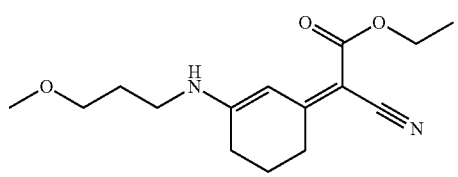 [SMILES: CCOC(=O)/C(C#N)=C1\C=C(NCCCOC)CCC1] |
| 15 | 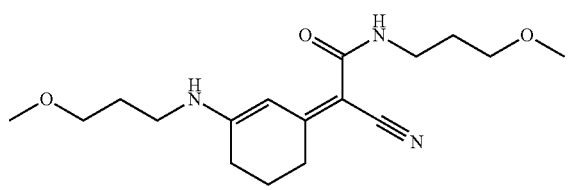 |
| 16 | 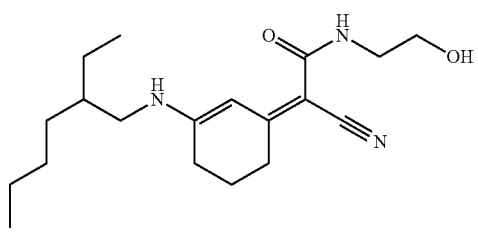 [SMILES: CCCCC(CC)CNC1=C/C(=C(/C#N)C(=O)NCCO)CCC1] |

TABLE A-continued
| Compound | Structure |
|---|---|
| 17 | 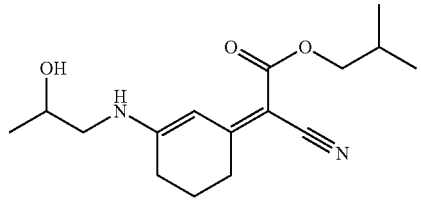 [SMILES: CC(C)COC(=O)/C(C#N)=C1\C=C(NCC(C)O)CCC1] |
| 18 | 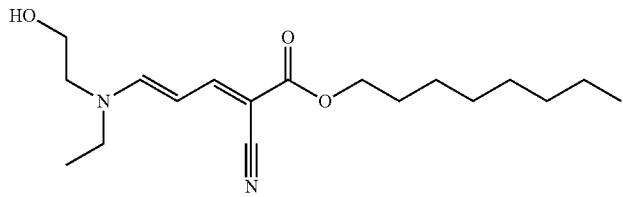 [SMILES: CCCCCCCCOC(=O)/C(C#N)=C/C=C/N(CC)CCO] |
| 19 | 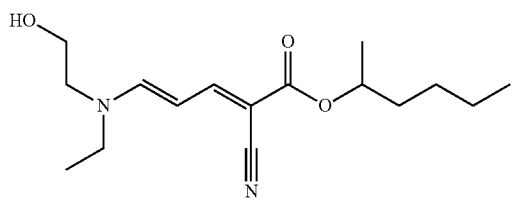 [SMILES: CCCCC(C)OC(=O)/C(C#N)=C/C=C/N(CC)CCO] |
| 20 | 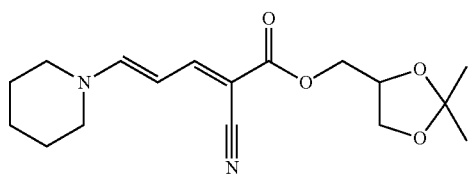 [SMILES: CC1(C)OCC(COC(=O)/C(C#N)=C/C=C/N2CCCCC2)O1] |
| 21 | 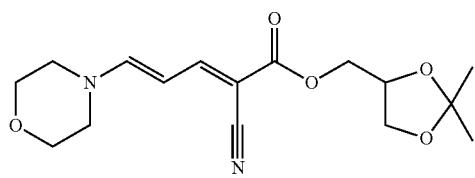 [SMILES: CC1(C)OCC(COC(=O)/C(C#N)=C/C=C/N2CCOCC2)O1] |
| 22 | 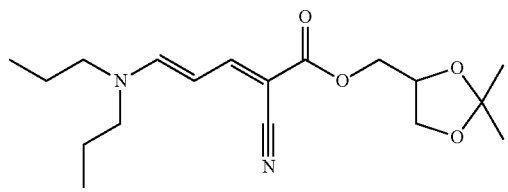 [SMILES: CCCN(/C=C/C=C(\C#N)C(=O)OCC1COC(C)(C)O1)CCC] |
| 23 | 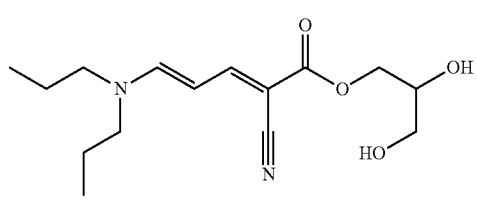 [SMILES: CCCN(/C=C/C=C(\C#N)C(=O)OCC(O)CO)CCC] |
| 24 | 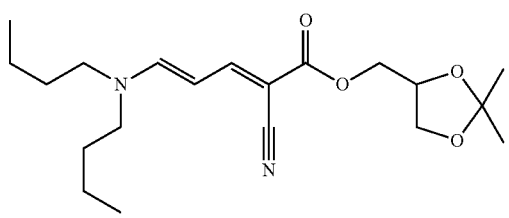 [SMILES: CCCCN(/C=C/C=C(\C#N)C(=O)OCC1COC(C)(C)O1)CCCC] |

TABLE A-continued

| Compound | Structure |
|---|---|
| 25 | 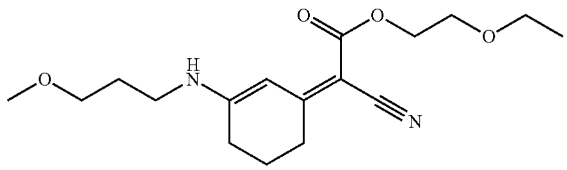 [SMILES: CCOCCOC(=O)/C(C#N)=C1\C=C(NCCCOC)CCC1] |
| 26 | 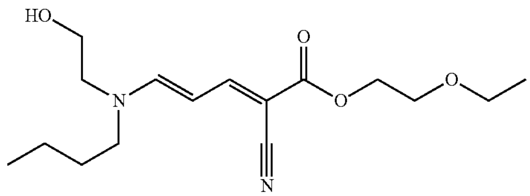 [SMILES: CCCCN(/C=C/C=C(\C#N)C(=O)OCCOCC)CCO] |
| 27 | 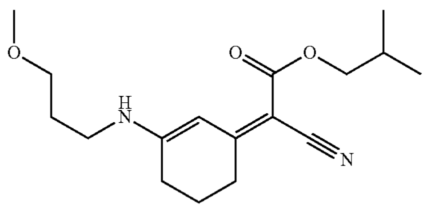 [SMILES: COCCCNC1=C/C(=C(/C#N)C(=O)OCC(C)C)CCC1] |
| 28 | 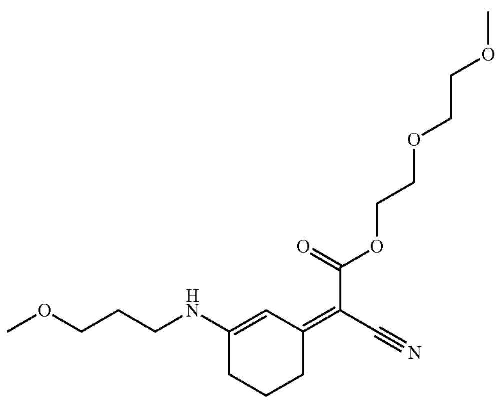 |
| 29 | 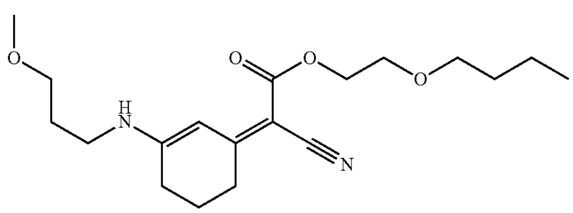 [SMILES: CCCCOCCOC(=O)/C(C#N)=C1\C=C(NCCCOC)CCC1] |
| 30 | 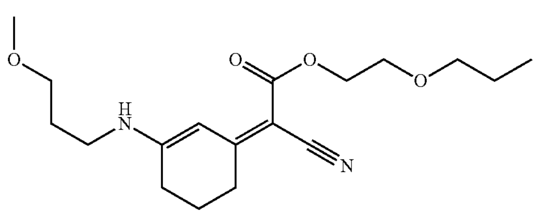 [SMILES: CCCOCCOC(=O)/C(C#N)=C1\C=C(NCCCOC)CCC1] |

TABLE A-continued
| Compound | Structure |
|---|---|
| 31 | 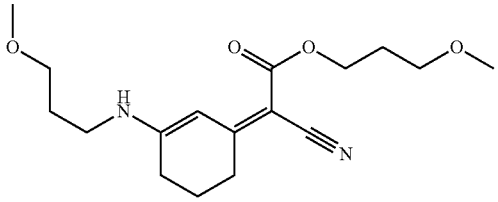 [SMILES: COCCCNC1=C/C(=C(/C#N)C(=O)OCCCOC)CCC1] |
| 32 | 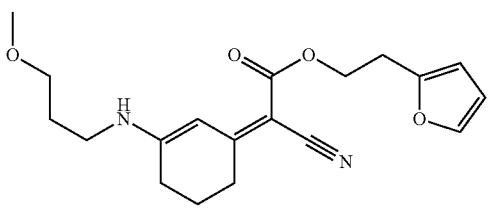 [SMILES: COCCCNC1=C/C(=C(/C#N)C(=O)OCCc2ccco2)CCC1] |
| 33 | 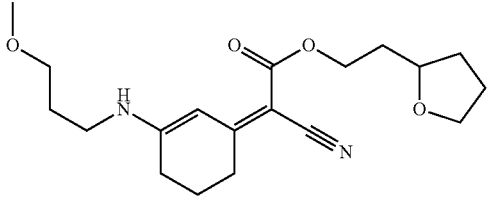 [SMILES: COCCCNC1=C/C(=C(/C#N)C(=O)OCCC2CCCO2)CCC1] |
| 34 | 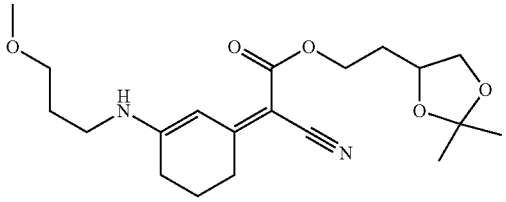 [SMILES: COCCCNC1=C/C(=C(/C#N)C(=O)OCCC2COC(C)(C)O2)CCC1] |
| 35 | 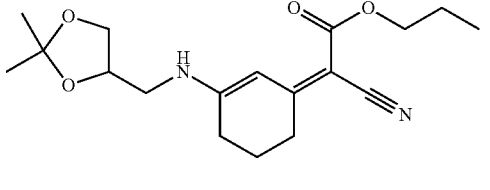 [SMILES: CCCOC(=O)/C(C#N)=C1\C=C(NCC2COC(C)(C)O2)CCC1] |
| 36 | 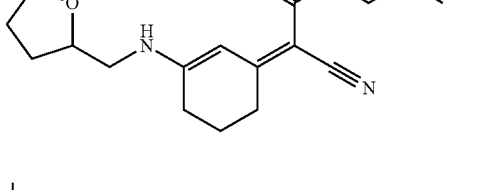 |
| 37 | 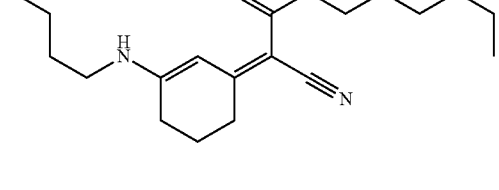 |

TABLE A-continued

| Compound | Structure |
|---|---|
| 38 | 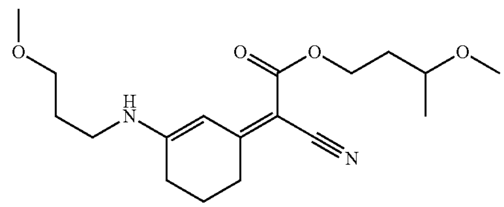 [SMILES: COCCCNC1=C/C(=C(/C#N)C(=O)OCCC(C)OC)CCC1] |
| 39 | 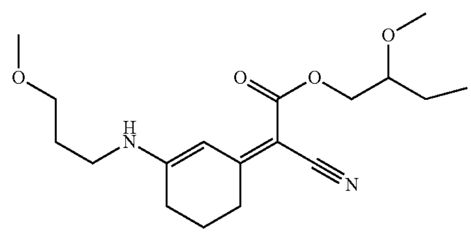 [SMILES: CCC(COC(=O)/C(C#N)=C1\C=C(NCCCOC)CCC1)OC] |
| 40 | 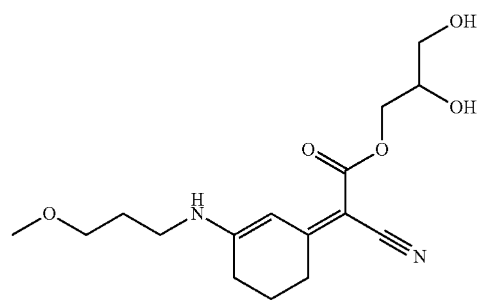 [SMILES: COCCCNC1=C/C(=C(/C#N)C(=O)OCC(O)CO)CCC1] |
| 41 | 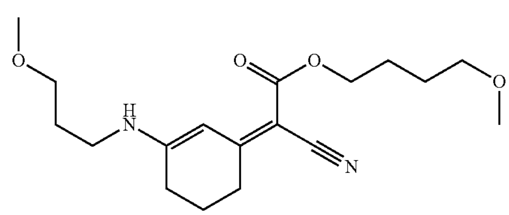 [SMILES: COCCCCOC(=O)/C(C#N)=C1\C=C(NCCCOC)CCC1] |
| 42 | 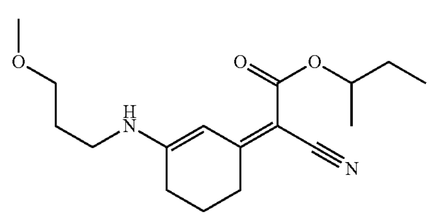 [SMILES: CCC(C)OC(=O)/C(C#N)=C1\C=C(NCCCOC)CCC1] |
| 43 | 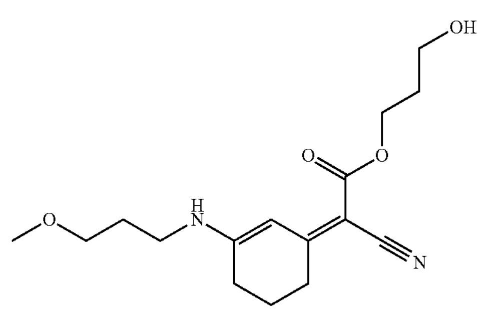 [SMILES: COCCCNC1=C/C(=C(/C#N)C(=O)OCCCO)CCC1] |

TABLE A-continued

| Compound | Structure |
|---|---|
| 44 | 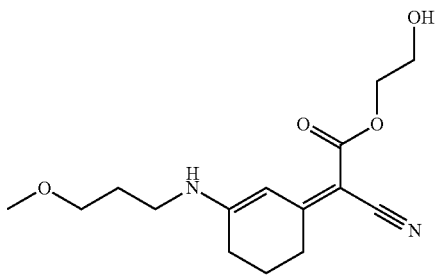 [SMILES: COCCCNC1=C/C(=C(/C#N)C(=O)OCCO)CCC1] |
| 45 | 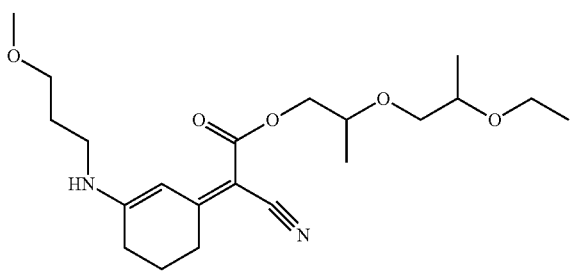 [SMILES: CCOC(C)COC(C)COC(=O)/C(C#N)=C1\C=C(NCCCOC)CCC1] |
| 46 | 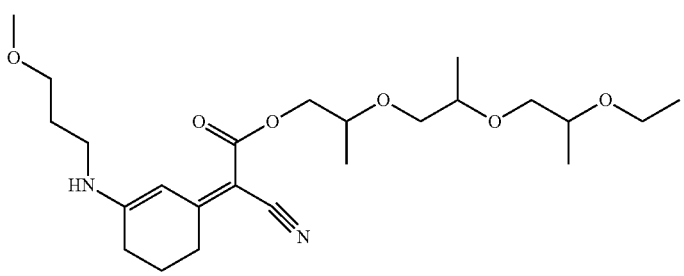 [SMILES: CCOC(C)COC(C)COC(C)COC(=O)/C(C#N)=C1\C=C(NCCCOC)CCC1] |
| 47 | 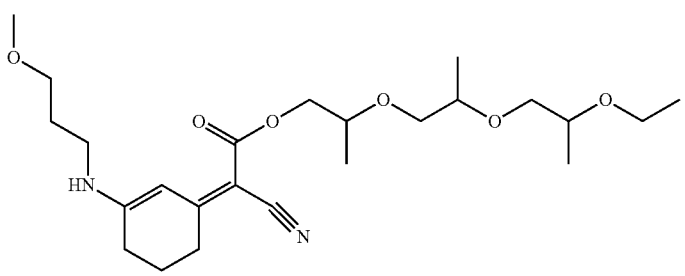 [SMILES: CCOC(C)COC(C)COC(C)COC(=O)/C(C#N)=C1\C=C(NCCCOC)CCC1] |

According to a particularly preferred form of the invention, use will be made of a family of merocyanines corresponding to formula (3) below, and also the E/E- or E/Z-geometrical isomer forms thereof:

in which

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, said groups possibly being interrupted with one or more O.

The merocyanine compounds of the invention may be in the E/E- or E/Z-geometrical isomer forms thereof.

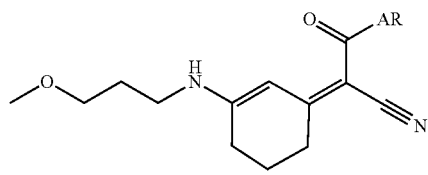
(3)

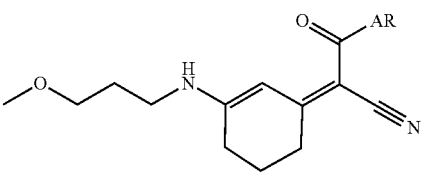

-continued

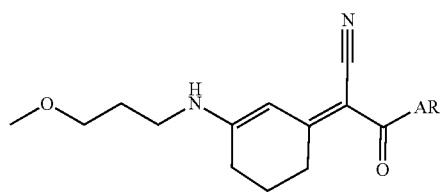

The compounds of formula (3) that are even more preferential are those in which:

A is -O—; R is a $C_1$-$C_{22}$ alkyl, which may be interrupted with one or more O.

Among the compounds of formula (3), use will be made more particularly of those chosen from the following group and also the E/E- or E/Z-geometrical isomer forms thereof:

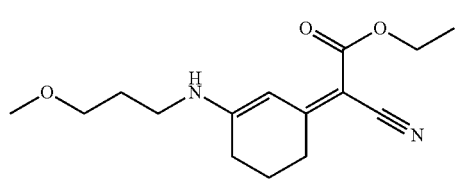

ethyl (2Z)-cyano{3-[(3-methoxypropyl)amino]cyclohex-2-en-1-ylidene}ethanoate

14

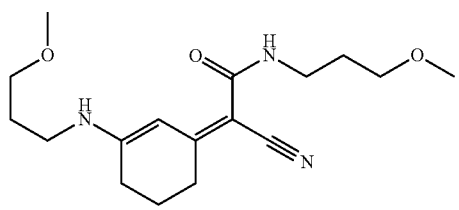

(2Z)-cyano-N-(3-methoxypropyl)-2-{3-[(3-methoxypropyl)amino]cyclohex-2-en-1-ylidene}ethanamide

25

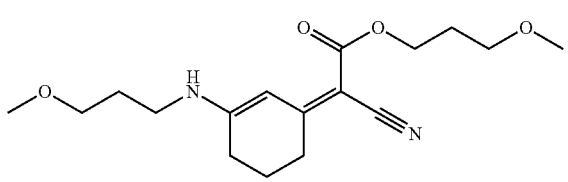

2-ethoxyethyl (2Z)-cyano{3-[(3-methoxypropyl)amino]cyclohex-2-en-1-ylidene}ethanoate

27

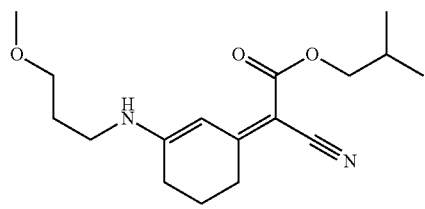

2-methylpropyl (2Z)-cyano{3-[(3-methoxypropyl)amino]cyclohex-2-en-1-ylidene}ethanoate -continued

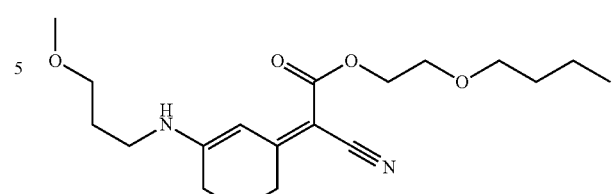

2-butoxyethyl (2Z)-cyano{3-[(3-methoxypropyl)amino]cyclohex-2-en-1-ylidene}ethanoate

29

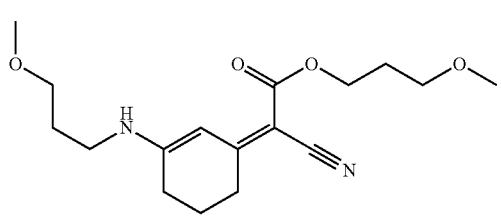

3-methoxypropyl (2Z)-cyano{3-[(3-methoxypropyl)amino]cyclohex-2-en-1-ylidene}ethanoate

31

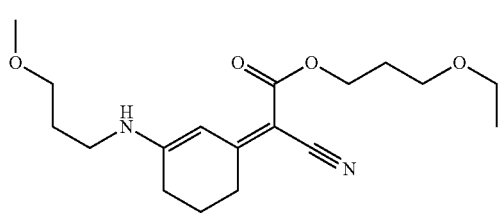

3-ethoxypropyl (2Z)-cyano{3-[(3-methoxypropyl)amino]cyclohex-2-en-1-ylidene}ethanoate

37

According to a more particularly preferred mode of the invention, use will be made of the compounds (14) and/or (25) and mixtures thereof and even particularly of the compound (25) in its E/E and/or E/Z geometrical configuration.

The E/Z form has the following structure:

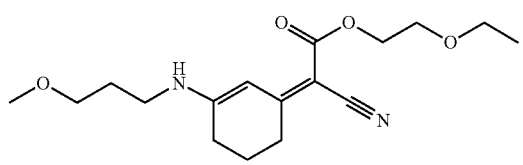 [SMILES: CCOCCOC(=O)/C(C#N)=C1\C=C(NCCCOC)CCC1]

The E/E form has the following structure:

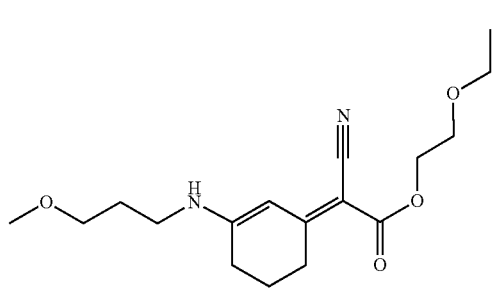 [SMILES: CCOCCOC(=O)/C(C#N)=C1/C=C(NCCCOC)CCC1]

The screening merocyanines in accordance with the invention may be present in the compositions according to the invention in a concentration ranging from 0.1% to 25% by weight, and preferentially from 0.2% to 20% by weight and better still from 0.5% to 10% by weight relative to the total weight of the composition.

The compounds of formulae (1) and (2) and especially of formula (3) may be prepared according to known processes, as described, for example, in J. Org. Chem. USSR (English Translation) 26(8), page 1562f (1990); J. Heterocycl. Chem. 33(3), pages 763-766 (1996); Khimiya Geterotsiklicheskikh Soedinenii 11, pages 1537-1543 (1984); Khimiya Geterotsiklicheskikh Soedinenii 3, pages 397-404 (1982); Chem. Heterocycl. Comp. (English Translation) 24(8), 914-919 (1988) and in Synthetic Communications Vol. 33, No. 3, 2003, p 367-371.

The synthesis of the compounds used in the present invention is also described in US2003/0181483A1, WO 0234710, Eur. J. Org. Chem. 2003, 2250-2253, J. Med. Chem. 1996, 39, 1112-1124 and J. Org. Chem., Vol. 37, No. 8, 1972, 1141-1145 as follows:

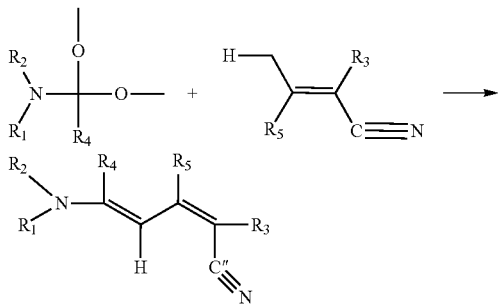

CH-acid vinylogen compounds are reacted with amide acetals.

In J. Heterocyclic Chem., 27, 1990, 1143-1151, aminoacrylic acid esters or aminoacrylonitriles are reacted with ethoxymethylenecyanoacetates in ethanol to form the corresponding compounds of the present invention.

The compounds of formula (1) or (2) in which $R_4$ and $R_5$, on the one hand, or $R_9$ and $R_{10}$, on the other hand, together form a carbocyclic ring containing 6 carbon atoms, respectively, may be prepared according to the protocols described in patent application WO 2007/071582, in IP.com Journal (2009), 9(5A), 29-30 IPCOM000182396D under the title "Process for producing 3-amino-2-cyclohexan-1-ylidene compounds" and in U.S. Pat. No. 4,749,643 on col. 13, line 66-col. 14, line 57 and the references cited in this regard.

Alkyl or Alkylene Carbonates

According to one embodiment, the alkylene chain(s) of the alkylene carbonate(s) and/or the alkyl radical(s) of the alkyl carbonate(s) present in the composition according to the invention comprise(s) from 1 to 6 carbon atoms, preferably from 2 to 6 carbon atoms, and more preferably from 2 to 4 carbon atoms, and are eventually substituted by one or more hydroxyl groups.

According to another embodiment, the sum of the carbons of the alkylene chain(s) of alkylene carbonate(s) and/or the sum of the carbons of the alkyl group(s) of the alkyl carbonate(s) present in the composition according to the invention is (are) ranging from 2 to 6 carbon atoms.

The alkylene carbonates are notably chosen from those of formula (4) below:

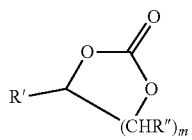

in which formula (4)
R' denotes a hydrogen atom, a linear or branched $C_1$-$C_6$ alkyl radical, a linear or branched $C_1$-$C_4$ hydroxyalkyl radical;
R" represents a hydrogen atom, a linear or branched $C_1$-$C_6$ alkyl radical, a linear or branched $C_1$-$C_4$ hydroxyalkyl radical;
m is 1, 2 or 3.

Preferably, the radical R' represents a hydrogen atom, a linear or branched $C_1$-$C_4$ alkyl radical, a linear or branched $C_1$-$C_2$ hydroxyalkyl radical.

R" represents a hydrogen atom, a linear or branched $C_1$-$C_2$ alkyl radical, a linear or branched $C_1$-$C_2$ hydroxyalkyl radical.

Preferably, m is 1.

As particularly advantageous examples of alkylene carbonates, mention may be made of the compounds for which the radical R' represents a hydrogen atom (corresponding to ethylene carbonate), a methyl group (corresponding to propylene carbonate), ethyl (corresponding to 1,2-butylene carbonate), hydroxymethyl (R'=—$CH_2OH$; corresponding to glyceryl carbonate).

Preferably, the alkylene carbonate used is propylene carbonate.

The alkyl carbonates are notably chosen from those of formula (5) below:

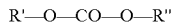

in which formula (5)
R' denotes a linear or branched $C_1$-$C_5$ alkyl radical, a linear or branched $C_1$-$C_4$ hydroxyalkyl radical;
R" represents a linear or branched $C_1$-$C_5$ alkyl radical, a linear or branched $C_1$-$C_4$ hydroxyalkyl radical;
the sum of the carbons of R' and R" ranging from 2 to 6.

Preferably, the radical R' represents a linear $C_1$-$C_3$ alkyl radical, a linear $C_1$-$C_2$ hydroxyalkyl radical.

R" represents a linear $C_1$-$C_3$ alkyl radical, a linear $C_1$-$C_2$ hydroxyalkyl radical.

More particularly, mention may be made of diethyl carbonate and dipropyl carbonate.

The carbonates according to the invention are preferably alkylene carbonates and more particularly propylene carbonate.

The alkyl or alkylene carbonates are present in the compositions according to the invention in concentrations preferably ranging from 0.1% to 98% by weight, particularly from 0.5% to 50% by weight, more preferentially from 1% to 20% by weight and even more particularly from 5% to 15% by weight relative to the total weight of the composition.

Oily Phase

The compositions in accordance with the invention comprise at least one oily phase.

For the purposes of the invention, the term "oily phase" means a phase comprising at least one oil and all of the liposoluble and lipophilic ingredients and the fatty substances used for the formulation of the compositions of the invention.

The term "oil" means any fatty substance that is in liquid form at room temperature (20-25° C.) and atmospheric pressure (760 mmHg).

The oily phase may comprise, besides the merocyanine screening agent(s) and optionally the additional lipophilic screening agents and the N,N-disubstituted amide(s) according to the invention, at least one volatile or non-volatile hydrocarbon-based oil and/or one volatile or non-volatile silicone oil and/or one volatile or non-volatile fluoro oil.

For the purposes of the present invention, the term "silicone oil" means an oil comprising at least one silicon atom, and especially at least one Si—O group.

The term "hydrocarbon-based oil" means an oil mainly containing hydrogen and carbon atoms and optionally one or more heteroatoms, in particular nitrogen and oxygen. Thus, these oils may notably contain one or more carboxyl, ester, ether or hydroxyl functions.

The term "fluoro oil" means an oil comprising at least one fluorine atom.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils, which are liquid at room temperature, having a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil that remains on the skin or the keratin fibre at room temperature and atmospheric pressure for at least several hours, and that especially has a vapour pressure of less than 10-3 mmHg (0.13 Pa).

Hydrocarbon-Based Oils

Mention may especially be made, as non-volatile hydrocarbon-based oils which may be used according to the invention, of:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheatgerm oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, sesame oil, marrow oil, blackcurrant oil, evening primrose oil, millet oil, barley oil, *quinoa* oil, rye oil, safflower oil, candlenut oil, passionflower oil and musk rose oil; or also caprylic/capric acid triglycerides, such as those sold by the company Stearinerie Dubois or those sold under the names Miglyol 810®, 812® and 818® by the company Dynamit Nobel;

(ii) synthetic ethers containing from 10 to 40 carbon atoms;

(iii) linear or branched hydrocarbons of mineral or synthetic origin, such as petroleum jelly, polydecenes, hydrogenated polyisobutene, such as Parleam, squalane and mixtures thereof;

(iv) synthetic esters, for instance oils of formula RCOOR' in which R represents the linear or branched fatty acid residue containing from 1 to 40 carbon atoms and R' represents a hydrocarbon-based chain that is in particular branched, containing from 1 to 40 carbon atoms, on condition that R+R' is ≥10, for instance purcellin oil (cetostearyl octanoate), isopropyl myristate, isopropyl palmitate, $C_{12}$-$C_{15}$ alkyl benzoate, such as the product sold under the trade name Finsolv TN® or Witconol TN® by the company Witco or Tegosoft TN® by the company Evonik Goldschmidt, 2-ethylphenyl benzoate, such as the commercial product sold under the name X-Tend 226® by the company ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name Dub Dis by the company Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by the company Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid; (vii) carbonates, such as dicaprylyl carbonate, such as the product sold under the name Cetiol CC® by the company Cognis;

and mixtures thereof.

Among the non-volatile hydrocarbon-based oils that may be used according to the invention, preference will be given more particularly to glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, in particular octyldodecanol.

As volatile hydrocarbon-based oils that may be used according to the invention, mention may be made in particular of hydrocarbon-based oils containing from 8 to 16 carbon atoms and especially of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched $C_8$-$C_{16}$ esters, isohexyl neopentanoate, and mixtures thereof.

Mention may also be made of the alkanes described in the Cognis patent applications WO 2007/068 371 or WO 2008/155 059 (mixtures of different alkanes differing by at least one carbon). These alkanes are obtained from fatty alcohols, which are themselves obtained from coconut kernel or palm oil. Mention may be made of the mixtures of n-undecane ($C_{11}$) and n-tridecane (013) obtained in Examples 1 and 2 of patent application WO 2008/155 059 from the company Cognis. Mention may also be made of n-dodecane (012) and n-tetradecane (014) sold by Sasol under the respective references Parafol 12-97 and Parafol 14-97®, and also mixtures thereof.

Other volatile hydrocarbon-based oils, for instance petroleum distillates, in particular those sold under the name Shell Solt® by the company Shell, may also be used. According to one embodiment, the volatile solvent is chosen from volatile hydrocarbon-based oils containing from 8 to 16 carbon atoms, and mixtures thereof.

b) Silicone Oils

The non-volatile silicone oils may be chosen especially from non-volatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Examples of volatile silicone oils that may be mentioned include volatile linear or cyclic silicone oils, in particular those with a viscosity 8 centistokes ($8 \times 10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general formula (I):

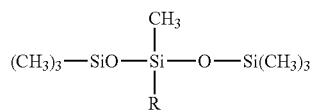

where R represents an alkyl group comprising from 2 to 4 carbon atoms, one or more hydrogen atoms of which may be replaced with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Fluoro Oils

Use may also be made of volatile fluoro oils, such as nonafluoromethoxybutane, decafluoropentane, tetradecafluorohexane, dodecafluoropentane, and mixtures thereof.

An oily phase according to the invention may also comprise other fatty substances, mixed with or dissolved in the oil.

Another fatty substance that may be present in the oily phase may be, for example:
a fatty acid chosen from fatty acids comprising from 8 to 30 carbon atoms, such as stearic acid, lauric acid, palmitic acid and oleic acid;
a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;
a gum chosen from silicone gums (dimethiconol);
a pasty compound, such as polymeric or non-polymeric silicone compounds, esters of a glycerol oligomer, arachidyl propionate, fatty acid triglycerides and derivatives thereof;
and mixtures thereof.

Preferentially, the overall oily phase, including all the lipophilic substances of the composition capable of being dissolved in this same phase, represents from 5% to 98% by weight and preferentially from 10% to 80% by weight, relative to the total weight of the composition.

Aqueous Phase

The compositions according to the invention may also comprise at least one aqueous phase.

An aqueous phase contains water and optionally other water-soluble or water-miscible organic solvents.

An aqueous phase that is suitable for use in the invention may comprise, for example, a water chosen from a natural spring water, such as waters from La Roche-Posay, water from Vittel, water from Saint-Gervais or waters from Vichy, or a floral water.

The water-soluble or water-miscible solvents that are suitable for use in the invention comprise short-chain, for example $C_1$-04, monoacohols such as ethanol and isopropanol; diols or polyols, such as ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may more particularly be made of ethanol, propylene glycol, glycerol, and mixtures thereof.

The water may represent from 5% to 95% by weight relative to the total weight of the composition.

According to one particular form of the invention, the overall aqueous phase, including all the hydrophilic substances of the composition which are capable of being dissolved in this same phase, represents from 5% to 95% by weight and preferably from 10% to 80% by weight relative to the total weight of the composition.

Additives a) Additional UV-Screening Agents:

The compositions according to the invention may also contain one or more additional UV-screening agents chosen from hydrophilic, lipophilic or insoluble organic UV-screening agents and/or one or more mineral pigments. It will preferentially be constituted of at least one hydrophilic, lipophilic or insoluble organic UV-screening agent.

The term "hydrophilic UV-screening agent" means any cosmetic or dermatological organic or inorganic compound for screening out UV radiation, which can be fully dissolved in molecular form in a liquid aqueous phase or which can be dissolved in colloidal form (for example in micellar form) in a liquid aqueous phase.

The term "lipophilic screening agent" means any cosmetic or dermatological organic or inorganic compound for screening out UV radiation, which can be fully dissolved in molecular form in a liquid fatty phase or which can be dissolved in colloidal form (for example in micellar form) in a liquid fatty phase.

The term "insoluble UV-screening agent" means any cosmetic or dermatological organic or inorganic compound for screening out UV radiation which has a solubility in water of less than 0.5% by weight and a solubility of less than 0.5% by weight in the majority of organic solvents such as liquid paraffin, fatty alcohol benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to room temperature. It may be readily evaluated in the laboratory.

The additional organic UV-screening agents are chosen in particular from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, in particular those cited in patent U.S. Pat. No. 5,624,663; benzimidazole derivatives; imidazoline compounds; bis-benzazolyl compounds, as described in patents EP 669 323 and U.S. Pat. No. 2,463,264; p-aminobenzoic (PABA) compounds; methylenebis(hydroxyphenylbenzotriazole) compounds, as described in patent applications U.S. Pat. Nos. 5,237,071, 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in patent application WO 93/04665; α-alkylstyrene-based dimers, such as those described in patent application DE 198 55 649; 4,4-diarylbutadiene compounds, as described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Cinnamic compounds:
Ethylhexyl methoxycinnamate sold in particular under the trade name Parsol MCX® by DSM Nutritional Products,
Isopropyl methoxycinnamate,
Isoamyl p-methoxycinnamate, sold under the trade name Neo Heliopan E 1000° by Symrise,
DEA methoxycinnamate,
Diisopropyl methylcinnamate,
Glyceryl ethylhexanoate dimethoxycinnamate.
Dibenzoyl methane compounds:
Butyl methoxydibenzoyl methane, sold in particular under the trade name Parsol 1789® by DSM Nutritial Products
Isopropyl dibenzoyl methane
para-Aminobenzoic compounds:
PABA,
Ethyl PABA,
Ethyl dihydroxypropyl PABA,
Ethylhexyl dimethyl PABA, sold in particular under the name Escalol 507® by ISP, Glyceryl PABA,
PEG-25 PABA, sold under the name Uvinul P 25® by BASF.
Salicylic compounds:
Homosalate, sold under the name Eusolex HMS® by Rona/EM Industries,
Ethylhexyl salicylate, sold under the name Neo Heliopan OS® by Symrise,
Dipropylene glycol salicylate, sold under the name Dipsal® by Scher,
TEA salicylate, sold under the name Neo Heliopan TS® by Symrise.
β, β-Diphenyl acrylate compounds:
Octocrylene, sold in particular under the trade name Uvinul N 539® by BASF,
Etocrylene, sold in particular under the trade name Uvinul N 35® by BASF.
Benzophenone compounds:
Benzophenone-1, sold under the trade name Uvinul 400® by BASF,
Benzophenone-2, sold under the trade name Uvinul D 50® by BASF,
Benzophenone-3 or Oxybenzone, sold under the trade name Uvinul M 40® by BASF,
Benzophenone-4, sold under the trade name Uvinul MS 40® by BASF,
Benzophenone-5,
Benzophenone-6, sold under the trade name Helisorb 11® by Norquay,
Benzophenone-8, sold under the trade name Spectra-Sorb UV-24® by American Cyanamid,
Benzophenone-9, sold under the trade name Uvinul DS 49° by BASF,
Benzophenone-12,
n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by the company BASF,
1,1'-(1,4-Piperazinediyl)bis[1-[2-[4-(diethylamino)-2-hydroxybenzoyl]phenyl]methanone] (CAS 919803-06-8), such as described in patent application WO 2007/071 584; this compound advantageously being used in micronized form (average size of 0.02 to 2 µm), which may be obtained, for example, according to the micronization process described in patent applications GB-A-2 303 549 and EP-A-893 119, and in particular in the form of an aqueous dispersion.

Benzylidenecamphor compounds:
3-Benzylidenecamphor, manufactured under the name Mexoryl SD® by Chimex,
4-Methylbenzylidenecamphor, sold under the name Eusolex 6300® by Merck,
Benzylidenecamphorsulfonic acid, manufactured under the name Mexoryl SL® by Chimex,
Camphor benzalkonium methosulfate, manufactured under the name Mexoryl SO® by Chimex,
Terephthalylidenedicamphorsulfonic acid, manufactured under the name Mexoryl SX® by Chimex,
Polyacrylamidomethylbenzylidenecamphor, manufactured under the name Mexoryl SW® by Chimex.
Phenylbenzimidazole compounds:
Phenylbenzimidazolesulfonic acid, sold in particular under the trade name Eusolex 232® by Merck.
Bis-benzoxazolyl compounds
Disodium phenyl dibenzimidazole tetrasulfonate, sold under the trade name Neo Heliopan AP® by Haarmann and Reimer.
Phenylbenzotriazole compounds:
Drometrizole trisiloxane, sold under the name Silatrizole® by Rhodia Chimie.
Methylenebis(hydroxyphenylbenzotriazole) compounds:
Methylenebis(benzotriazolyl)tetramethylbutylphenol, in particular in solid form, such as the product sold under the trade name Mixxim BB/1000® by Fairmount Chemical, or in the form of an aqueous dispersion of micronized particles with an average particle size ranging from 0.01 to 5 µm, more preferentially from 0.01 to 2 µm and more particularly from 0.020 to 2 µm, with at least one alkylpolyglycoside surfactant having the structure $C_nH_{2n+1}O$ $(C_6H_{10}O_5)_xH$, in which n is an integer from 8 to 16 and x is the mean degree of polymerization of the $(C_6H_{10}O_5)$ unit and ranges from 1.4 to 1.6, as described in patent GB-A-2 303 549, sold in particular under the trade name Tinosorb M® by the company BASF, or in the form of an aqueous dispersion of micronized particles with an average particle size ranging from 0.02 to 2 µm, more preferentially from 0.01 to 1.5 µm and more particularly from 0.02 to 1 µm, in the presence of at least one polyglyceryl mono($C_8$-$C_{20}$)alkyl ester with a degree of glycerol polymerization of at least 5, such as the aqueous dispersions described in patent application WO 2009/063 392.
Triazine compounds:
Bis-ethylhexyloxyphenol methoxyphenyl triazine, sold under the trade name Tinosorb S® by BASF, Ethylhexyl triazone, sold in particular under the trade name Uvinul T150® by BASF, Diethylhexyl butamido triazone, sold under the trade name Uvasorb HEB® by Sigma 3V, 2,4,6-Tris(dineopentyl 4'-aminobenzalmalonate)-s-triazine, 2,4,6-Tris(diisobutyl 4'-aminobenzalmalonate)-s-triazine, 2,4-bis(n-butyl 4'-aminobenzoate)-6-(aminopropyltrisiloxane)-s-triazine, 2,4-bis(dineopentyl 4'-aminobenzalmalonate)-6-(n-butyl 4'-aminobenzoate)-s-triazine, symmetrical triazine screening agents substituted with naphthalenyl groups or polyphenyl groups described in patent U.S. Pat. No. 6,225,467, patent application WO 2004/085 412 (see compounds 6 and 9) or the document "Symmetrical Triazine Derivatives", IP.COM IPCOM000031257 Journal, INC West Henrietta, NY, US (20 Sep. 2004), in particular 2,4,6-tris(diphenyl) triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 μm), which may be obtained, for example, according to the micronization process described in patent applications GB-A-2 303 549 and EP-A-893 119, and in particular in aqueous dispersion form, silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyloxy] disiloxanyl}propyl)amino]-s-triazine.

Anthranilic compounds:

Menthyl anthranilate, sold under the trade name Neo Heliopan MA® by Symrise.

Imidazoline compounds:

Ethylhexyl dimethoxybenzylidene dioxoimidazoline propionate.

Benzalmalonate compounds:

Polyorganosiloxane comprising benzalmalonate functions, such as Polysilicone-15, sold under the trade name Parsol SLX® by Hoffmann-LaRoche.

4,4-Diarylbutadiene compounds:

1,1-Dicarboxy(2,2'-dimethylpropyl)-4,4-diphenylbutadiene.

Benzoxazole compounds:

2,4-Bis[5-1(dimethylpropyl)benzoxazol-2-yl(4-phenyl) imino]-6-(2-ethylhexyl)imino-1,3,5-triazine, sold under the name Uvasorb K2A® by Sigma 3V.

The preferential organic screening agents are chosen from:

Ethylhexyl methoxycinnamate

Ethylhexyl salicylate,

Homosalate,

Butyl methoxydibenzoyl methane,

Octocrylene,

Phenylbenzimidazolesulfonic acid,

Benzophenone-3,

Benzophenone-4,

Benzophenone-5, n-Hexyl 2-(4-diethylamino-2-hydroxybenzoyl)benzoate,

4-Methylbenzylidenecamphor,

Terephthalylidenedicamphorsulfonic acid,

Disodium phenyldibenzimidazoletetrasulfonate,

Methylenebis(benzotriazolyl)tetramethylbutylphenol,

Bis-ethylhexyloxyphenol methoxyphenyl triazine,

Ethylhexyl triazone

Diethylhexyl butamidotriazone, 2,4,6-Tris(dineopentyl 4'-aminobenzalmalonate)-s-triazine, 2,4,6-Tris(diisobutyl 4'-aminobenzalmalonate)-s-triazine, 2,4-Bis(n-butyl 4'-aminobenzoate)-6-(aminopropyltrisiloxane)-s-triazine, 2,4-Bis(dineopentyl 4'-aminobenzalmalonate)-6-(n-butyl 4'-aminobenzoate)-s-triazine, 2,4-Bis(n-butyl 4'-aminobenzalmalonate)-6-[(3-{1,3,3,3-tetramethyl-1-[(trimethylsilyl)oxy]disiloxanyl}propyl) amino]-s-triazine, 2,4,6-Tris(diphenyl)triazine, 2,4,6-Tris(terphenyl)triazine, Drometrizole trisiloxane, Polysilicone-15, 1,1-Dicarboxy(2,2'-dimethylpropyl)-4,4-diphenylbutadiene, 2,4-bis[5-(1-Dimethylpropyl)benzoxazol-2-yl-(4-phenyl) imino]-6-(2-ethylhexyl)imino-1,3,5-triazine, and mixtures thereof.

The particularly preferred organic screening agents are chosen from:

Ethylhexyl salicylate,

Homosalate,

Butyl methoxydibenzoyl methane,

Octocrylene, n-Hexyl 2-(4-diethylamino-2-hydroxybenzoyl)benzoate,

Terephthalylidenedicamphorsulfonic acid,

Bis-ethylhexyloxyphenol methoxyphenyl triazine,

Ethylhexyl triazone,

Diethylhexyl butamidotriazone, 2,4-Bis(n-butyl 4'-aminobenzalmalonate)-6-[(3-{1,3,3,3-tetramethyl-1-[(trimethylsilyl)oxy]disiloxanyl}propyl) amino]-s-triazine, Drometrizole trisiloxane, and mixtures thereof.

The inorganic UV-screening agents used in accordance with the present invention are metal oxide pigments. More preferentially, the inorganic UV-screening agents of the invention are metal oxide particles with a mean elementary particle size of less than or equal to 0.5 μm, more preferentially between 0.005 and 0.5 μm, even more preferentially between 0.01 and 0.2 μm, better still between 0.01 and 0.1 μm and more particularly between 0.015 and 0.05 μm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:

with silica, such as the product Sunveil® from the company Ikeda, with silica and iron oxide, such as the product Sunveil F® from the company Ikeda, with silica and alumina, such as the products Microtitanium Dioxide MT 500 SA® and Microtitanium Dioxide MT 100 SA from the company Tayca and Tioveil from the company Tioxide, with alumina, such as the products Tipaque TTO-55 (B)® and Tipaque TTO-55 (A)® from the company Ishihara and UVT 14/4 from the company Sachtleben Pigments, with alumina and aluminium stearate, such as the products Microtitanium Dioxide MT 100 T®, MT 100 TX®, MT 100 Z® and MT-01® from the company Tayca, the products Solaveil CT-10 W® and Solaveil CT 100® from the company Uniqema and the product Eusolex T-AVO® from the company Merck, with silica, alumina and alginic acid, such as the product MT-100 AQ® from the company Tayca, with alumina and aluminium laurate, such as the product Microtitanium Dioxide MT 100 S® from the company Tayca, with iron oxide and iron stearate, such as the product Microtitanium Dioxide MT 100 F® from the company Tayca, with zinc oxide and zinc stearate, such as the product BR 351® from the company Tayca, with silica and alumina and treated with a silicone, such as the products Microtitanium Dioxide MT 600 SAS®, Microtitanium Dioxide MT 500 SAS® or Microtitanium Dioxide MT 100 SAS® from the company Tayca, with silica, alumina and aluminium stearate and treated with a silicone, such as the product STT-30-DS® from the company Titan Kogyo, with silica and treated with a silicone, such as the product UV-Titan X 195® from the company Sachtleben Pigments, with alumina and treated with a silicone, such as the products Tipaque TTO-55 (S)® from the company Ishihara or UV Titan M 262® from the company Sachtleben Pigments, with triethanolamine, such as the product STT-65-S from the company Titan Kogyo, with stearic acid, such as the product Tipaque TTO-55 (C)® from the company Ishihara, with sodium hexametaphosphate, such as the product Microtitanium Dioxide MT 150 W® from the company Tayca, $TiO_2$ treated with octyltrimethylsilane, sold under the trade name T 805® from the company Degussa Silices, $TiO_2$ treated with a polydimethylsiloxane, sold under the trade name 70250 Cardre UF $TiO_2SI3$® by the company Cardre, anatase/rutile $TiO_2$ treated with a polydimethylhydrogenosiloxane, sold under the trade name Microtitanium Dioxide USP Grade Hydrophobic® by the company Color Techniques.

$TiO_2$ coated with triethylhexanoin, aluminium stearate and alumina, sold under the trade name Solaveil CT-200-LQ-(WD) from Croda, $TiO_2$ coated with aluminum stearate, alumina and silicone, sold under the trade name Solaveil CT-12W-LQ-(WD from Croda), $TiO_2$ coated with lauroyl lysine, sold by Daito Kasei Kogyo under the name LL 5 Titanium Dioxide CR 50, $TiO_2$ coated with $C_9$-15 fluoroalcohol phosphate and aluminium hydroxide, sold by Daito Casei Kogyo under the name PFX-5 $TiO_2$ CR-50.

Mention may also be made of $TiO_2$ pigments doped with at least one transition metal such as iron, zinc or manganese and more particularly manganese. Preferably, said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG-3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of $TiO_2$ particles doped with manganese in capric/caprylic acid triglyceride in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wacker under the name Transparent titanium oxide PW®, by the company Miyoshi Kasei under the name UFTR®, by the company Tomen under the name ITS® and by the company Tioxide under the name Tioveil AQ.

The uncoated zinc oxide pigments are, for example:
those sold under the name Z-Cote by the company Sunsmart;
those sold under the name Nanox® by the company Elementis;
those sold under the name Nanogard WCD 2025® by the company Nanophase Technologies.

The coated zinc oxide pigments are, for example:
those sold under the name Zinc Oxide CS-5® by the company Toshibi (ZnO coated with polymethylhydrogenosiloxane);
those sold under the name Nanogard Zinc Oxide FN® by the company Nanophase Technologies (as a 40% dispersion in Finsolv TN®, $C_{12}$-$C_{15}$ alkyl benzoate);
those sold under the name Daitopersion Zn-30® and Daitopersion Zn-50® by the company Daito (dispersions in cyclopolymethylsiloxane/oxyethylenated polydimethylsiloxane, containing 30% or 50% of zinc oxides coated with silica and polymethylhydrogenosiloxane);
those sold under the name NFD Ultrafine ZnO® by the company Daikin (ZnO coated with perfluoroalkyl phosphate and copolymer based on perfluoroalkylethyl as a dispersion in cyclopentasiloxane);
those sold under the name SPD-Z1® by the company Shin-Etsu (ZnO coated with silicone-grafted acrylic polymer, dispersed in cyclodimethylsiloxane); those sold under the name Escalol Z100® by the company ISP (alumina-treated ZnO dispersed in the ethylhexyl methoxycinnamate/PVP-hexadecene copolymer/methicone mixture);
those sold under the name Fuji ZnO-SMS-100® by the company Fuji Pigment (ZnO coated with silica and polymethylsilsesquioxane);
those sold under the name Nanox Gel TN® by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company Rhône-Poulenc.

The uncoated iron oxide pigments are sold, for example, by the company Arnaud under the names Nanogard WCD 2002® (FE 45B®), Nanogard Iron FE 45 BL AQ, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, especially of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

The additional UV-screening agents according to the invention are preferably present in the compositions according to the invention in a content ranging from 0.1% to 60% by weight and in particular from 5% to 30% by weight relative to the total weight of the composition.

b) Other Additives:

The compositions in accordance with the present invention may also comprise conventional cosmetic adjuvants chosen in particular from organic solvents, ionic or nonionic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, basifying or acidifying agents or any other ingredient commonly used in the cosmetic and/or dermatological field.

Mention may be made, among organic solvents, of alcohols other than $C_1$-$C_4$ monoalkanols as defined above and in particular short-chain $C_2$-$C_8$ polyols, such as glycerol or diols, such as caprylyl glycol, 1,2-pentanediol, propanediol, butanediol, glycols and glycol ethers, such as ethylene glycol, propylene glycol, butylene glycol, dipropylene glycol or diethylene glycol.

Mention may be made, as thickeners, of carboxyvinyl polymers, such as the Carbopols® (Carbomers) and the Pemulens, such as Pemulen TR1® and Pemulen TR2® (acrylate/$C_{10}$-$C_{30}$ alkyl acrylate copolymer); polyacrylamides, for instance the crosslinked copolymers sold under the names Sepigel 305® (CTFA name: polyacrylamide/$C_{13}$-14 isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS® (CTFA name: ammonium polyacryloyldimethyl taurate or Simulgel 800® sold by the company SEPPIC (CTFA name: sodium polyacryolyldimethyl taurate/polysorbate 80/sorbitan oleate); copolymers of 2-acrylamido-2-methylpropanesulfonic acid and of hydroxyethyl acrylate, for instance Simulgel NS® and Sepinov EMT 10® sold by the company SEPPIC; cellulose derivatives such as hydroxyethyl cellulose; polysaccharides and especially gums such as xanthan gum; water-soluble or water-dispersible silicone derivatives, for instance acrylic silicones, polyether silicones and cationic silicones, and mixtures thereof.

Among the acidifying agents that may be mentioned, by way of example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, alkanolamines, such as mono-, di- and triethanolamines and derivatives thereof, sodium hydroxide or potassium hydroxide.

Preferably, the cosmetic composition comprises one or more basifying agents chosen from alkanolamines, in particular triethanolamine, and sodium hydroxide.

In the case of a direct emulsion, the pH of the composition in accordance with the invention is generally between 3 and 12 approximately, preferably between 5 and 11 approximately and even more particularly from 6 to 8.5.

Among the active agents for caring for keratin materials such as the skin, the lips, the scalp, the hair, the eyelashes or the nails, examples that may be mentioned include:

vitamins and derivatives or precursors thereof, alone or as mixtures;
antioxidants;
free-radical scavengers;
antipollution agents;
self-tanning agents;
antiglycation agents;
calmatives;
deodorants;
essential oils;
NO-synthase inhibitors;
agents for stimulating the synthesis of dermal or epidermal macromolecules and/or for preventing their degradation;
agents for stimulating fibroblast proliferation;
agents for stimulating keratinocyte proliferation;
muscle relaxants;
refreshing agents;
tensioning agents;
matt-effect agents;
depigmenting agents;
pro-pigmenting agents;
keratolytic agents;
desquamating agents;
moisturizers;
anti-inflammatory agents;
antimicrobial agents;
slimming agents;
agents that act on the energy metabolism of cells;
insect repellents;
substance P or CGRP antagonists;
hair-loss counteractants;
antiwrinkle agents;
antiageing agents.

A person skilled in the art will select said active agent(s) as a function of the effect desired on the skin, the hair, the eyelashes, the eyebrows and the nails.

Needless to say, those skilled in the art will take care to select the abovementioned optional additional compound(s) and/or the amounts thereof so that the advantageous properties intrinsically associated with the compositions in accordance with the invention are not, or not substantially, adversely affected by the envisaged addition(s).

According to a preferred embodiment of the invention, the composition comprises: a) at least a merocyanine corresponding to formula (3) and also the E/E- or E/Z-geometrical isomer forms:

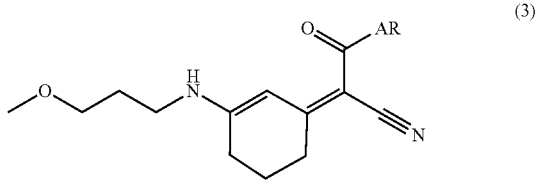

in which:

A is —O— or —NH;

R is a C1-C22 alkyl group, a C2-C22 alkenyl group, a C2-C22 alkynyl group, a C3-C22 cycloalkyl group or a C3-C22 cycloalkenyl group, said groups possibly being interrupted with one or more O;

b) at least one oily phase comprising at least one alkyl or alkylene carbonate, present in concentrations preferably ranging from 0.1% to 98% by weight, preferably from 0.5% to 50% by weight and more preferentially from 1% to 20% by weight relative to the total weight of the composition.

Presentation Forms

The compositions according to the invention may be prepared according to the techniques that are well known to those skilled in the art. They may in particular be in the form of a simple or complex emulsion (O/W, W/O, O/W/O or W/O/W), such as a cream, a milk or a cream gel.

They may also be in anhydrous form, for instance in the form of an oil. The term "anhydrous composition" means a composition containing less than 1% by weight of water, or even less than 0.5% water, and especially free of water, the water not being added during the preparation of the composition but corresponding to the residual water provided by the mixed ingredients. They may optionally be packaged in aerosol form and may be in the form of a mousse or a spray.

In the case of compositions in the form of oil-in-water or water-in-oil emulsions, the emulsification processes that may be used are of the paddle or impeller, rotor-stator and HPH type.

The emulsions generally contain at least one emulsifier chosen from amphoteric, anionic, cationic or nonionic emulsifiers, used alone or as a mixture, preferably nonionic emulsifiers. The emulsifiers are chosen in an appropriate manner according to the emulsion to be obtained (W/O or O/W emulsion).

When it is an emulsion, the aqueous phase of this emulsion may comprise a nonionic vesicular dispersion prepared according to known processes (Bangham, Standish and Watkins, J. Mol. Biol. 13, 238 (1965), FR 2 315 991 and FR 2 416 008).

The compositions according to the invention find their application in a large number of treatments, in particular cosmetic treatments, for the skin, the lips and the hair, including the scalp, in particular for protecting and/or caring for the skin, the lips and/or the hair, and/or for making up the skin and/or the lips.

Another subject of the present invention is constituted of the use of the compositions according to the invention as defined above for the manufacture of products for the cosmetic treatment of the skin, the lips, the nails, the hair, the eyelashes, the eyebrows and/or the scalp, in particular care products, antisun products and makeup products.

The cosmetic compositions according to the invention may be used, for example, as makeup products.

Another subject of the present invention is constituted of a non-therapeutic cosmetic process for caring for and/or making up a keratin material, which consists in applying, to the surface of said keratin material, at least one composition according to the invention as defined above.

The cosmetic compositions according to the invention may be used, for example, as care products and/or antisun products for the face and/or body, with a liquid to semi-liquid consistency, such as milks, more or less smooth creams, gel-creams, pastes or lotions. They may optionally be packaged in aerosol form and may be in the form of a mousse or a spray.

The compositions according to the invention in the form of vaporizable fluid lotions in accordance with the invention are applied to the skin or hair in the form of fine particles by means of pressurizing devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

Assembly

According to another aspect, the invention also relates to a cosmetic assembly comprising:

i) a container delimiting one or more compartment(s), said container being closed by a closing member and optionally being unsealed; and ii) a makeup and/or care composition in accordance with the invention placed inside said compartment(s).

The container may be, for example, in the form of a jar or a box.

The closing member may be in the form of a lid comprising a cap mounted so as to be able to move by translation or by pivoting relative to the container housing said makeup and/or care composition(s).

The examples that follow serve to illustrate the invention without, however, being limiting in nature. In these examples, the amounts of the composition ingredients are given as weight percentages relative to the total weight of the composition.

EXAMPLES

Protocol for evaluating solubility

The solubility of merocyanine in the oily solutions is evaluated macroscopically and microscopically. It is considered that the merocyanine is soluble if, at room temperature, the solution appears to the eye to be clear and translucent, and it does not have any visible crystals under a white-light or polarized-light microscope (objective ×20 to ×40). The solubility is evaluated at room temperature, on the day of preparation of the solution and then over time. During this time period, the solutions are stored at room temperature and/or at 4° C., away from the light.

Examples 1-6: Oily Compositions

The following oily compositions were prepared according to the process below.

| Ingredients | Example 1 (according to the invention) | Example 2 (outside the invention) | Example 3 (outside the invention) |
|---|---|---|---|
| Compound (25) | 10 | 10 | 10 |
| Propylene carbonate | 90 | — | — |
| Isopropyl lauroyl sarcosinate (Eldew 205 from Ajinomoto) | — | — | 90 |
| Dicaprylyl carbonate (Cetiol CC from BASF) | — | 90 | — |
| Solubility at room temperature | >2 months | Insoluble | 14 days |
| Solubility at 4° C. | >2 months | Insoluble | 7 days |

| Ingredients | Example 4 (according to the invention) | Example 5 (outside the invention) | Example 6 (outside the invention) |
|---|---|---|---|
| Compound (14) | 10 | 10 | 10 |
| Propylene carbonate | 90 | — | — |
| Isopropyl lauroyl sarcosinate (Eldew 205 from Ajinomoto) | — | — | 90 |
| Dicaprylyl carbonate (Cetiol CC from BASF) | — | 90 | — |
| Solubility at room temperature | >2 months | Insoluble | 14 days |
| Solubility at 4° C. | 1 month | Insoluble | 3 days |

Examples 7-12: Oleo-Alcoholic Compositions

The following compositions were prepared according to the above process.

| Ingredients | Example 7 (according to the invention) | Example 8 (outside the invention) | Example 9 (outside the invention) |
|---|---|---|---|
| Merocyanine compound (25) | 17 | 17 | 17 |
| Propylene carbonate | 41.5 | — | — |
| Isopropyl lauroyl sarcosinate (Eldew 205 from Ajinomoto) | — | — | 41.5 |
| Dicaprylyl carbonate (Cetiol CC from BASF) | — | 41.5 | — |
| Ethanol | 41.5 | 41.5 | 41.5 |
| Solubility at room temperature | >2 months | 1 day | 1 day |
| Solubility at 4° C. | >2 months | 1 day | 1 day |

| Ingredients | Example 10 (according to the invention) | Example 11 (outside the invention) | Example 12 (outside the invention) |
|---|---|---|---|
| Merocyanine compound (14) | 17 | 17 | 17 |
| Propylene carbonate | 41.5 | — | — |
| Isopropyl lauroyl sarcosinate (Eldew 205 from Ajinomoto) | — | — | 41.5 |
| Dicaprylyl carbonate (Cetiol CC from BASF) | — | 41.5 | — |
| Ethanol | 41.5 | 41.5 | 41.5 |
| Solubility at room temperature | >2 months | >2 months | >2 months |
| Solubility at 4° C. | >2 months | 3 days | 3 days |

Examples 13-15: Oleo-Alcoholic Compositions

The following compositions were prepared according to the process below.

| Ingredients | Example 13 (according to the invention) | Example 14 (outside the invention) | Example 15 (outside the invention) |
|---|---|---|---|
| Merocyanine compound (25) | 20 | 20 | 20 |
| Propylene carbonate | 40 | — | — |
| Isopropyl lauroyl sarcosinate (Eldew 205 from Ajinomoto) | — | 40 | — |
| Dicaprylyl carbonate (BASF) | — | — | 40 |
| Ethanol | 40 | 40 | 40 |
| Solubility at room temperature | >2 months | 1 day | 1 day |
| Solubility at 4° C. | >2 months | 1 day | 1 day |

Process for preparing the oils:

The compositions described in Examples 1 and 15 are prepared in the following manner: the screening agent and the oil are successively introduced into a container and are then stirred using a magnetic stirrer and heated at 90° C. for between 10 minutes and 1 hour, until the merocyanine has dissolved.

Examples 16-17: Reverse Emulsion Compositions

The following compositions were prepared:

| Ingredients | Example 16 (according to the invention) | Example 17 (outside the invention) |
|---|---|---|
| Polyglyceryl Polyricinoleate | 3.75 | 3.75 |
| Dioctyl oxide | 7.5 | 7.5 |
| Isopropyl palmitate | 7.5 | 7.5 |
| Isohexadecane | 7.5 | 7.5 |
| Isocetyl yl stearate | 7.5 | 7.5 |
| Octane-1,2-diol | 0.5 | 0.5 |
| Anisic acid | 0.15 | 0.15 |
| Propylene carbonate | 5 | — |
| Isopropyl lauroyl sarcosinate (Eldew 205 from Ajinomoto) | — | 5 |
| Hectorite modified with stearylbenzyldimethylammonium | 1 | 1 |
| Merocyanine compound (25) | 1 | 1 |
| Deionized water | qs 100% | qs 100% |
| Glycerol | 6 | 6 |
| Pentane-1,2-diol | 2 | 2 |
| Propane-1,3-diol | 3 | 3 |
| Citric acid monohydrate | 0.1 | 0.1 |
| Ethanol | 5 | 5 |
| Solubility at room temperature | >1 month | 14 days |
| Solubility at 4° C. | >1 month | 14 days |

These results show that the alkyl or alkylene carbonate according to the invention make it possible to maintain the solubility of the merocyanine over time at room temperature and at low temperature.

The invention claimed is:

1. A cosmetic or dermatological composition comprising:
    a) at least one merocyanine corresponding to either of formulae (1) and (2) below or an E/E- or E/Z-geometrical isomer form thereof:

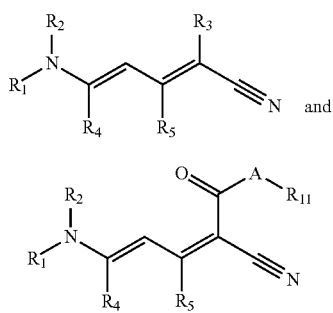

(1)

(2)

in which:
R$_1$ and R$_2$, independently of each other, are hydrogen; a C$_1$-C$_{22}$ alkyl group, a C$_2$-C$_{22}$ alkenyl group, or a C$_2$-C$_{22}$ alkynyl group, these groups possibly being substituted with at least one hydroxyl group or else interrupted with at least one —O—; or else R$_1$ and R$_2$ form, together with the nitrogen atom which links them, a —(CH$_2$)$_n$— ring which may be optionally interrupted with —O— or —NH—;

R$_3$ is a —(C=O)OR$_6$ group; or a —(CO)NHR$_6$ group;

R$_6$ is a C$_1$-C$_{22}$ alkyl group, a C$_2$-C$_{22}$ alkenyl group, a C$_2$-C$_{22}$ alkynyl group, a C$_3$-C$_{22}$ cycloalkyl group or a C$_3$-C$_{22}$ cycloalkenyl group, said groups possibly being substituted with one or more OH;

R$_4$ and R$_5$ are hydrogens; or R$_4$ and R$_5$ form a —(CH$_2$)$_n$— ring which may be substituted with a C$_1$-C$_4$ alkyl group and/or interrupted with one or more —O— or with —NH—;

R$_7$ and R$_8$, independently of each other, are hydrogen; a C$_1$-C$_{22}$ alkyl group, a C$_2$-C$_{22}$ alkenyl group, a C$_2$-C$_{22}$ alkynyl group, said groups possibly being interrupted with one or more O and/or substituted with one or more OH; a C$_3$-C$_{22}$ cycloalkyl group or a C$_3$-C$_{22}$ cycloalkenyl group, said groups possibly being interrupted with one or more —O—;

or else R$_7$ and R$_8$ form, together with the nitrogen which links them, a —(CH$_2$)$_n$ ring which may be interrupted with one or more —O—;

R$_9$ and R$_{10}$ are hydrogen; or R$_9$ and R$_{10}$ form a —(CH$_2$)$_n$— ring potentially substituted with a C$_1$-C$_4$ alkyl and/or interrupted with an —O— or —NH—;

A is —O—; or —NH;

R$_{11}$ is a C$_1$-C$_{22}$ alkyl group; a C$_2$-C$_{22}$ alkenyl group; a C$_2$-C$_{22}$ alkynyl group; a C$_3$-C$_{22}$ cycloalkyl group or a C$_3$-C$_{22}$ cycloalkenyl group, said groups possibly being interrupted with one or more O; or a C$_1$-C$_{22}$ alkyl group or a C$_2$-C$_{22}$ alkenyl group which is substituted with a C$_3$-C$_{22}$ cycloalkyl group or a C$_3$-C$_{22}$ cycloalkenyl group, said C$_3$-C$_{22}$ cycloalkyl group or C$_3$-C$_{22}$ cycloalkenyl group possibly being interrupted with one or more —O—;

n is a number between 2 and 7; and, b) at least one oily phase comprising at least one alkyl or alkylene carbonate.

2. The composition according to claim 1, in which the compounds of formula (1) are chosen from those for which:
R$_6$ is a C$_1$-C$_{12}$ alkyl group, which may be substituted with one or more hydroxyls.

3. The composition according to claim 1 in which the compounds of formula (1) are chosen from those for which:
R$_6$ is a C$_1$-C$_{12}$ alkyl group, which may be substituted with one or more hydroxyls;

one of the R$_1$ or R$_2$ radicals is a C$_4$-C$_{22}$ alkyl group; or else R$_1$ and R$_2$ form, together with the nitrogen which links them, a —(CH$_2$)$_n$— ring which may be interrupted with —O— and/or —NH—; and R$_4$ and R$_5$ and n have the same meanings indicated in claim 1.

4. The composition according to claim 1, in which the compounds of formula (2) are chosen from those for which:
R$_{11}$ is a —(CH$_2$)$_m$—O—R$_{12}$ radical, in which
R$_{12}$ is a C$_1$-C$_{12}$ alkyl group; or a C$_1$-C$_6$ alkoxy-C$_1$-C$_6$ alkyl group;
m is a number from 1 to 5.

5. The composition according to claim 1, in which the compounds of formula (1) or (2) are chosen from those for which:
R$_1$ and R$_2$, on the one hand, and R$_7$ and R$_8$, on the other hand, respectively form, together with the nitrogen atom to which they are respectively bonded, a piperidyl radical or a morpholinyl radical.

6. The composition according to claim 1, in which the compounds of formula (1) or (2) are chosen from those for which:
R$_4$ and R$_5$ and R$_9$ and R$_{10}$ respectively form a carbon-based ring which contains 6 carbon atoms.

7. The composition according to claim 1, in which the compounds of formula (1) are chosen from those for which:
R$_1$ and R$_2$, independently of each other, are hydrogen; or a C$_1$-C$_{22}$ alkyl group; or a C$_1$-C$_{22}$ hydroxyalkyl group; or R$_1$ and R$_2$ form, together with the nitrogen atom to which they are bonded, a piperidyl or morpholinyl radical;

R$_3$ is a —(C=O)OR$_6$ group; or a —(CO)NHR$_6$ group;

R$_6$ is a C$_1$-C$_{22}$ alkyl group, which may be substituted with one or more —OH;

R$_4$ and R$_5$ are hydrogen; or R$_4$ and R$_5$ are linked together to form a carbon-based ring which contains 6 carbon atoms.

8. The composition according to claim 1, in which the compounds of formula (1) are chosen from those for which:
R$_1$ and R$_2$, independently of each other, are a hydrogen; or a C$_1$-C$_{22}$ hydroxyalkyl group; in which at least one of the R$_1$ and R$_2$ radicals is a C$_1$-C$_{22}$ hydroxyalkyl group;

R$_3$ is a —(C=O)OR$_6$ group; or a —(C=O)NHR$_6$ group;

R$_6$ is a C$_1$-C$_{12}$ alkyl group;

R$_4$ and R$_5$ are hydrogens; or R$_4$ and R$_5$ are bonded together to form a carbon-based ring which contains 6 carbon atoms.

9. The composition according to claim 1, in which the compounds of formula (2) are chosen from those for which:
R$_7$ and R$_8$, independently of each other, are a hydrogen or a C$_1$-C$_8$ alkyl group, which may be interrupted with one or more —O—;

A is —O— or —NH;

R$_{11}$ is a C$_1$-C$_{22}$ alkyl; and

R$_9$ and R$_{10}$ are a hydrogen; or R$_9$ and R$_{10}$ are bonded together to form a carbon-based ring which contains 6 carbon atoms.

10. The composition according to claim 1, in which the compounds of formula (2) are chosen from those for which:
R$_7$ and R$_8$ form, together with the nitrogen atom to which they are bonded, a morpholinyl or piperidyl radical;

A is —O—; or —NH;

R$_H$ is a C$_1$-C$_{22}$ alkyl group, which may be interrupted with one or more —O—; and $R_9$ and $R_{10}$ are hydrogens; or $R_9$ and $R_{10}$ are bonded together to form a carbon-based ring which contains 6 carbon atoms.

11. The composition according to claim 1, in which the compounds of formula (2) are chosen from those for which:
$R_{11}$ is a —$(CH_2)_m$—O—$R_{12}$ radical, in which
$R_{12}$ is a $C_1$-$C_4$ alkyl group; or a $C_1$-$C_4$ alkoxy-$C_1$-$C_4$ alkyl group;
m is a number from 1 to 3; and
$R_7$ and $R_8$, independently of each other, are hydrogen; or a $C_1$-$C_{12}$ alkyl group, which may be interrupted with one or more O; or $R_7$ and $R_8$ form, together with the nitrogen atom to which they are bonded, a morpholinyl or piperidyl radical;
$R_9$ and $R_{10}$ are hydrogens or together form a carbon-based ring which contains 6 carbon atoms; and
A is —O— or —NH.

12. The composition according to claim 1, in which the compounds of formula (1) or (2) are chosen from the following compounds and also the E/E- or E/Z-geometrical isomer forms thereof:

TABLE A

| Compound | Structure |
|---|---|
| 1 | 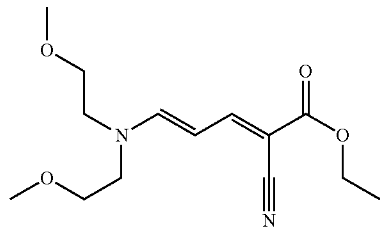 [SMILES: CCOC(=O)/C(C#N)=C/C=C/N(CCOC)CCOC] |
| 2 | 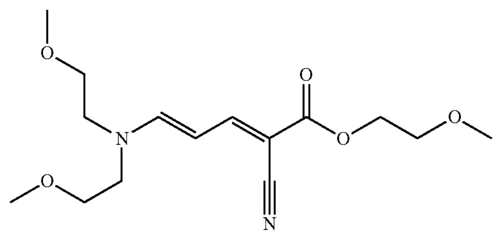 |
| 3 | 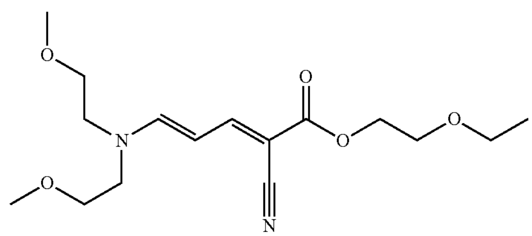 [SMILES: CCOCCOC(=O)/C(C#N)=C/C=C/N(CCOC)CCOC] |
| 4 | 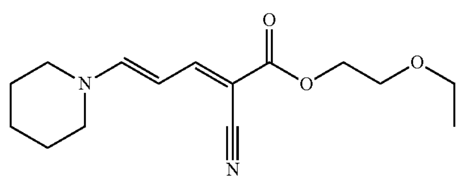 [SMILES: CCOCCOC(=O)/C(C#N)=C/C=C/N1CCCCC1] |
| 5 | 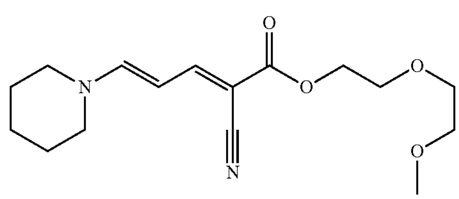 [SMILES: COCCOCCOC(=O)/C(C#N)=C/C=C/N1CCCCC1] |
| 6 | 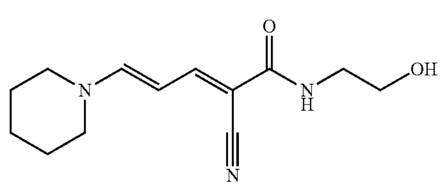 [SMILES: N#C/C(=C\C=C\N1CCCCC1)C(=O)NCCO] |

TABLE A-continued
| Compound | Structure |
|---|---|
| 7 | 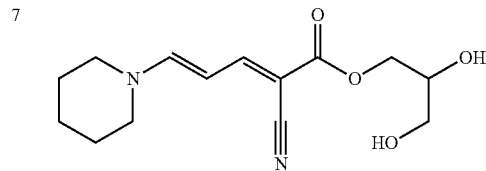 |
| 8 | 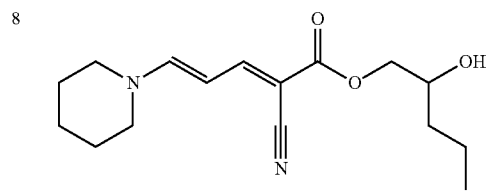 |
| 9 | 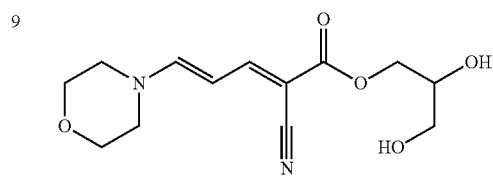 |
| 10 | 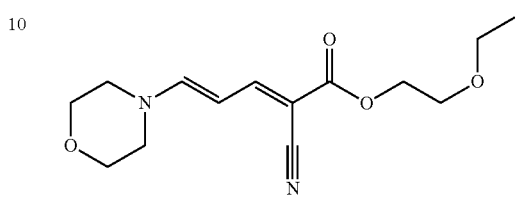 |
| 11 | 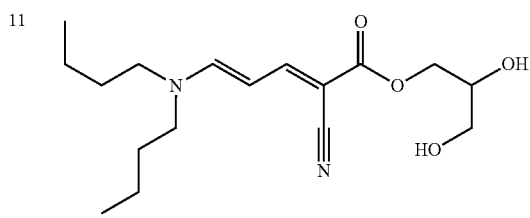 |
| 12 | 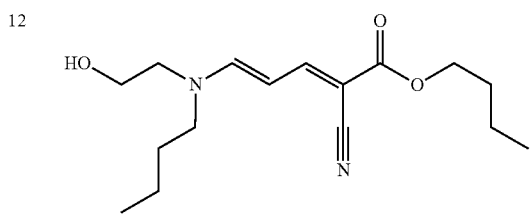 |
| 13 | 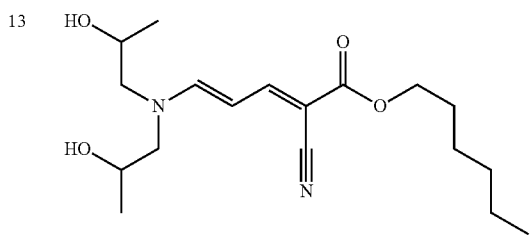 |
| 14 | 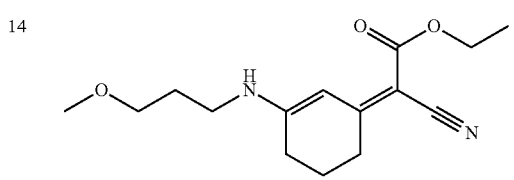 |

TABLE A-continued
| Compound | Structure |
|---|---|
| 15 | 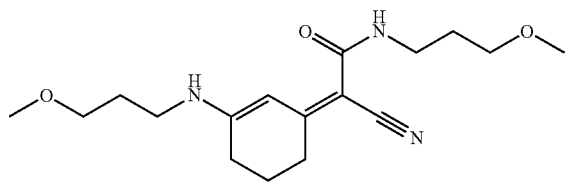 |
| 16 | 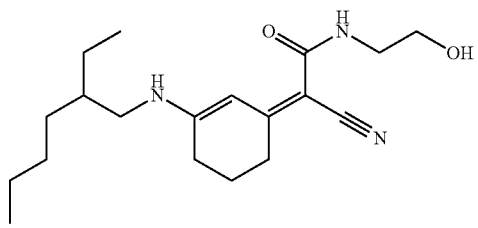 [SMILES: CCCCC(CC)CNC1=C/C(=C(/C#N)C(=O)NCCO)CCC1] |
| 17 | 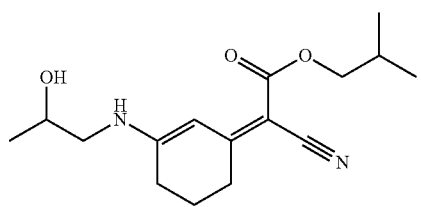 [SMILES: CC(C)COC(=O)/C(C#N)=C1\C=C(NCC(C)O)CCC1] |
| 18 | 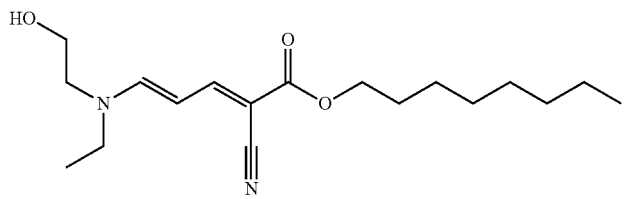 [SMILES: CCCCCCCCOC(=O)/C(C#N)=C/C=C/N(CC)CCO] |
| 19 | 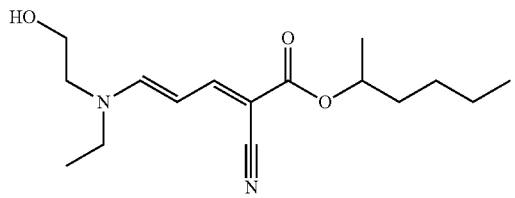 [SMILES: CCCCC(C)OC(=O)/C(C#N)=C/C=C/N(CC)CCO] |
| 20 | 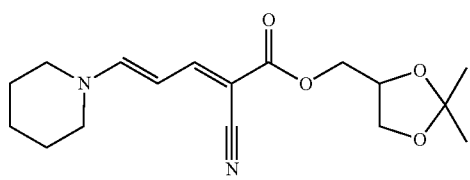 [SMILES: CC1(C)OCC(COC(=O)/C(C#N)=C/C=C/N2CCCCC2)O1] |
| 21 | 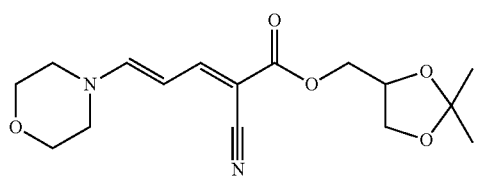 [SMILES: CC1(C)OCC(COC(=O)/C(C#N)=C/C=C/N2CCOCC2)O1] |

TABLE A-continued
| Compound | Structure |
|---|---|
| 22 | 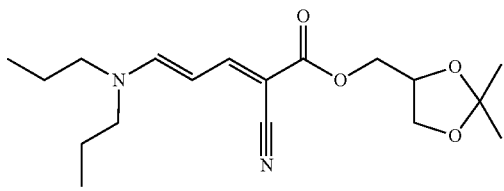 [SMILES: CCCN(/C=C/C=C(\C#N)C(=O)OCC1COC(C)(C)O1)CCC] |
| 23 | 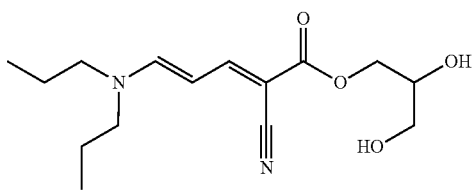 [SMILES: CCCN(/C=C/C=C(\C#N)C(=O)OCC(O)CO)CCC] |
| 24 | 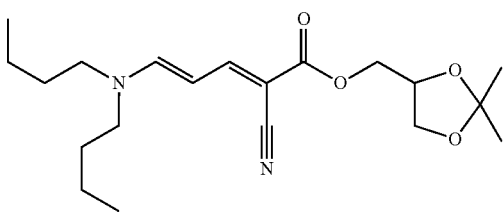 [SMILES: CCCCN(/C=C/C=C(\C#N)C(=O)OCC1COC(C)(C)O1)CCCC] |
| 25 | 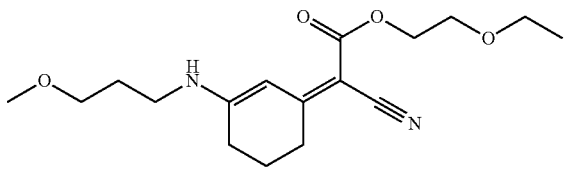 [SMILES: CCOCCOC(=O)/C(C#N)=C1\C=C(NCCCOC)CCC1] |
| 26 | 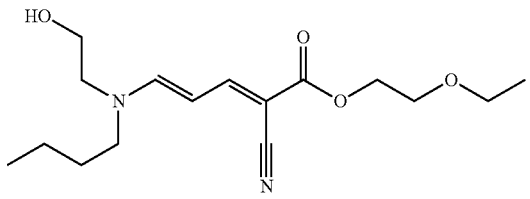 [SMILES: CCCCN(/C=C/C=C(\C#N)C(=O)OCCOCC)CCO] |
| 27 | 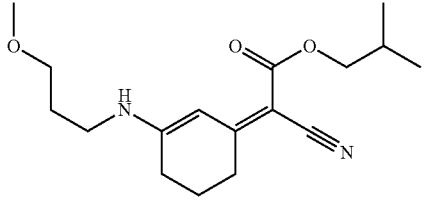 [SMILES: COCCCNC1=C/C(=C(/C#N)C(=O)OCC(C)C)CCC1] |
| 28 | 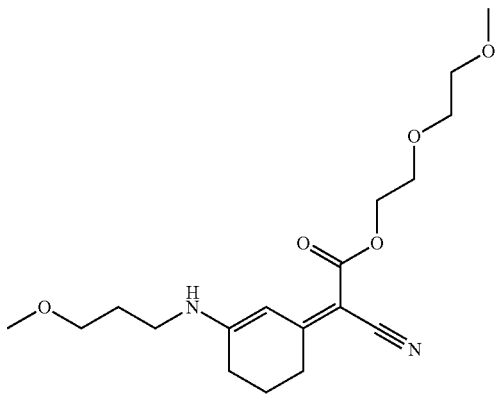 |

TABLE A-continued
| Compound | Structure |
|---|---|
| 29 | 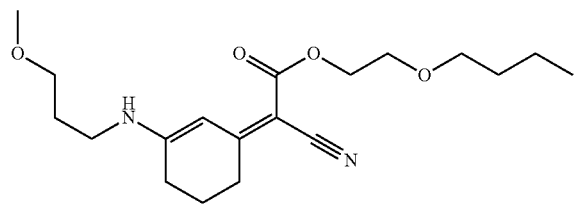 [SMILES: CCCCOCCOC(=O)/C(C#N)=C1\C=C(NCCCOC)CCC1] |
| 30 | 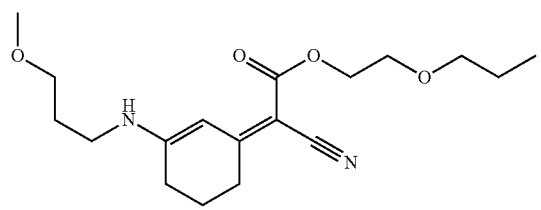 [SMILES: CCCOCCOC(=O)/C(C#N)=C1\C=C(NCCCOC)CCC1] |
| 31 | 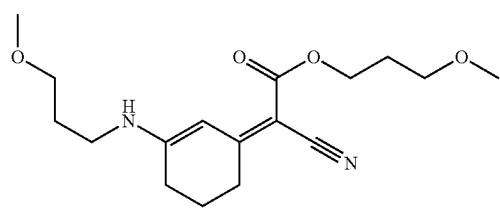 [SMILES: COCCCNC1=C/C(=C(/C#N)C(=O)OCCCOC)CCC1] |
| 32 | 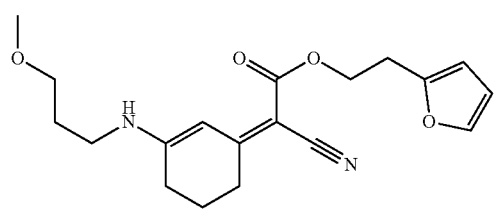 [SMILES: COCCCNC1=C/C(=C(/C#N)C(=O)OCCc2ccco2)CCC1] |
| 33 | 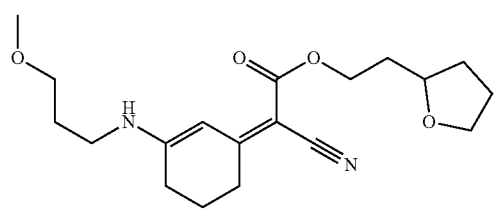 [SMILES: COCCCNC1=C/C(=C(/C#N)C(=O)OCCC2CCCO2)CCC1] |
| 34 | 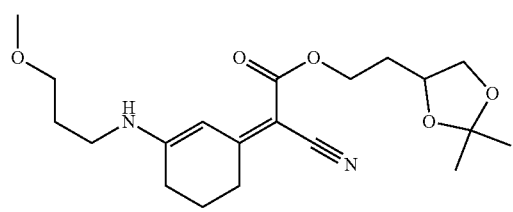 |
| 35 | 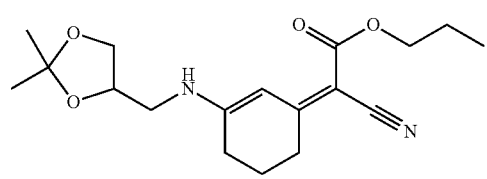 [SMILES: CCCOC(=O)/C(C#N)=C1\C=C(NCC2COC(C)(C)O2)CCC1] |

TABLE A-continued
| Compound | Structure |
|---|---|
| 36 | 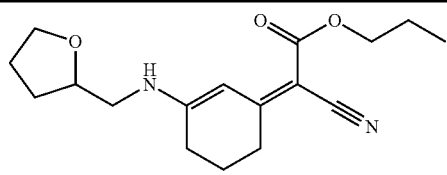 |
| 37 | 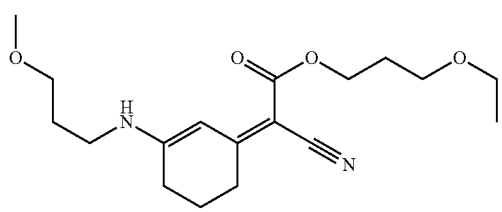 [SMILES: CCOCCCOC(=O)/C(C#N)=C1\C=C(NCCCOC)CCC1] |
| 38 | 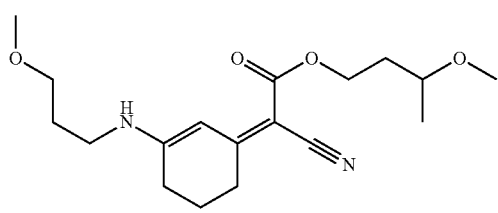 [SMILES: COCCCNC1=C/C(=C(/C#N)C(=O)OCCC(C)OC)CCC1] |
| 39 | 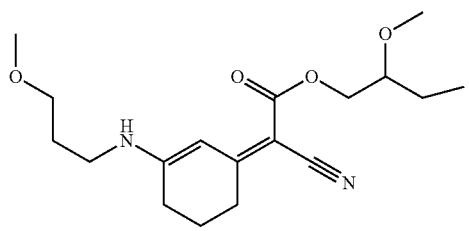 [SMILES: CCC(COC(=O)/C(C#N)=C1\C=C(NCCCOC)CCC1)OC] |
| 40 | 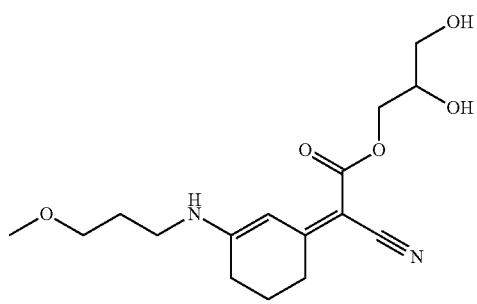 [SMILES: COCCCNC1=C/C(=C(/C#N)C(=O)OCC(O)CO)CCC1] |
| 41 | 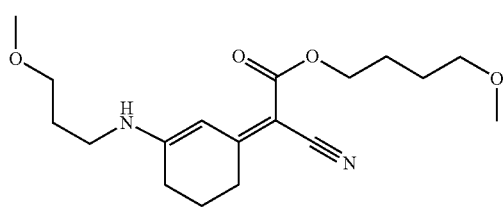 [SMILES: COCCCCOC(=O)/C(C#N)=C1\C=C(NCCCOC)CCC1] |
| 42 | 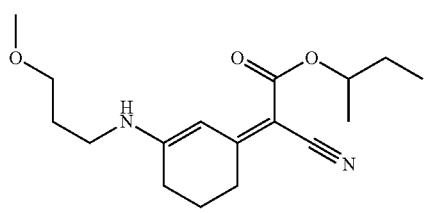 [SMILES: CCC(C)OC(=O)/C(C#N)=C1\C=C(NCCCOC)CCC1] |

TABLE A-continued
| Compound | Structure |
|---|---|
| 43 | 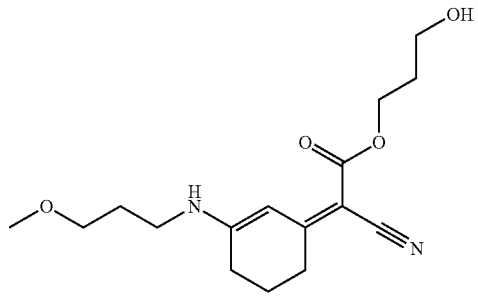 [SMILES: COCCCNC1=C/C(=C(/C#N)C(=O)OCCCO)CCC1] |
| 44 | 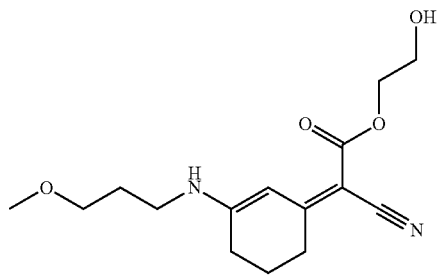 [SMILES: COCCCNC1=C/C(=C(/C#N)C(=O)OCCO)CCC1] |
| 45 | 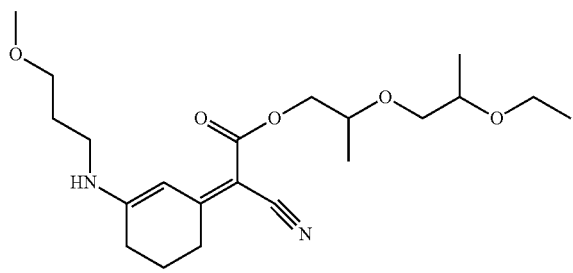 [SMILES: CCOC(C)COC(C)COC(=O)/C(C#N)=C1\C=C(NCCCOC)CCC1] |
| 46 | 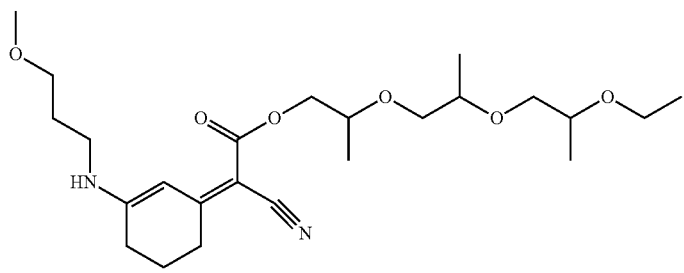 [SMILES: CCOC(C)COC(C)COC(C)COC(=O)/C(C#N)=C1\C=C(NCCCOC)CCC1] |
| 47 | 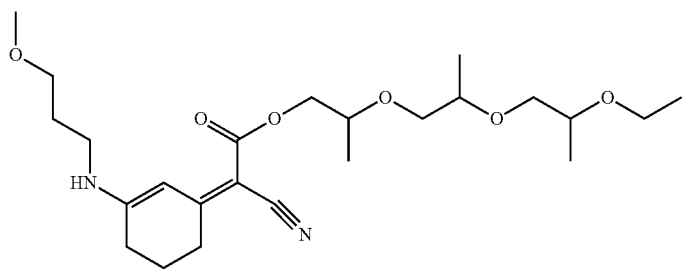 [SMILES: CCOC(C)COC(C)COC(C)COC(=O)/C(C#N)=C1\C=C(NCCCOC)CCC1] |

13. The composition according to claim 1, in which the compounds of formula (1) or (2) are chosen from those corresponding to formula (3) below and also the E/E- or E/Z-geometrical isomer forms thereof:

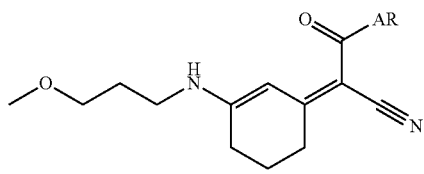
(3)

in which

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, said groups possibly being interrupted with one or more O.

14. The composition according to claim 13, in which the merocyanines of formula (3) are chosen from the following compounds and also the E/E- or E/Z-geometrical isomer forms thereof:

14

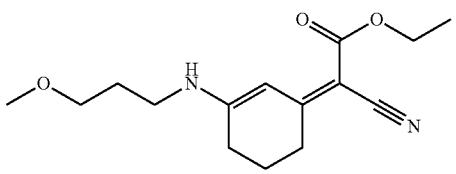 [SMILES: CCOC(=O)/C(C#N)=C1\C=C(NCCCOC)CCC1]

ethyl (2Z)-cyano{3-[(3-methoxypropyl)amino]cyclohex-2-en-1-ylidene}ethanoate

15

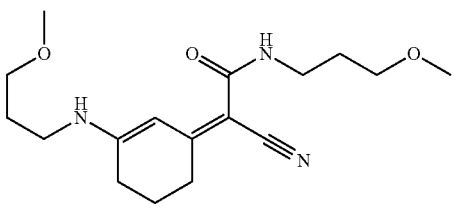 [SMILES: COCCCNC(=O)/C(C#N)=C1\C=C(NCCCOC)CCC1]

(2Z)-2-cyano-N-(3-methoxypropyl)-2-{3-[(3-methoxypropyl)amino]cyclohex-2-en-1-ylidene}ethanamide

25

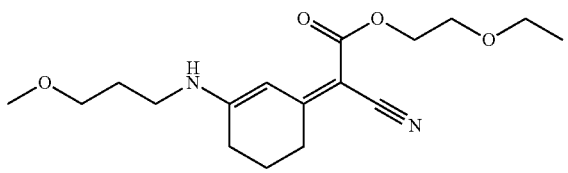 [SMILES: CCOCCOC(=O)/C(C#N)=C1\C=C(NCCCOC)CCC1]

2-ethoxyethyl (2Z)-cyano{3-[(3-methoxypropyl)amino]cyclohex-2-en-1-ylidene}ethanoate

27

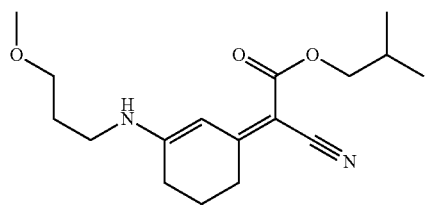 [SMILES: COCCCNC1=C/C(=C(/C#N)C(=O)OCC(C)C)CCC1]

2-methylpropyl (2Z)-cyano{3-[(3-methoxypropyl)amino]cyclohex-2-en-1-ylidene}ethanoate

29

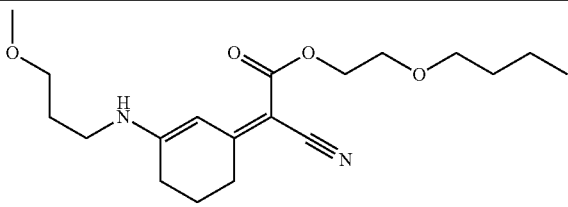

2-butoxyethyl (2Z)-cyano{3-[(3-methoxypropyl)amino]cyclohex-2-en-1-ylidene}ethanoate

31

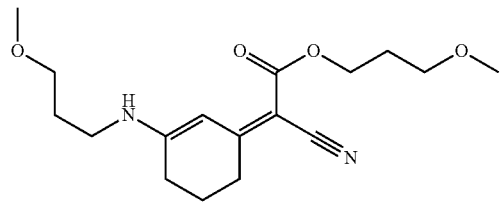 [SMILES: COCCCNC1=C/C(=C(/C#N)C(=O)OCCCOC)CCC1]

3-methoxypropyl (2Z)-cyano{3-[(3-methoxypropyl)amino]cyclohex-2-en-1-ylidene}ethanoate

37

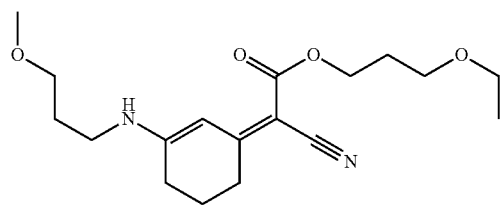 [SMILES: CCOCCCOC(=O)/C(C#N)=C1\C=C(NCCCOC)CCC1]

3-ethoxypropyl (2Z)-cyano{3-[(3-methoxypropyl)amino]cyclohex-2-en-1-ylidene}ethanoate 15. The composition according to claim 14, in which the merocyanine of formula (3) is chosen from the compound 2-ethoxyethyl (2Z)-cyano{3-[(3-methoxypropyl)amino]cyclohex-2-en-1-ylidene}ethanoate (25) and/or the compound ethyl (2Z)-cyano[3-[(3-methoxypropyl)amino]cyclohex-2-en-1-ylidene]ethanoate (14) and mixtures thereof and preferably the compound (25).

16. The composition according to claim 1, in which the merocyanine(s) are present in a concentration ranging from 0.1% to 25% by weight relative to the total weight of the composition.

17. The composition or dermatological composition according to claim 1, comprising:
a) at least a merocyanine corresponding to formula (3) and also the E/E- or E/Z-geometrical isomer forms:

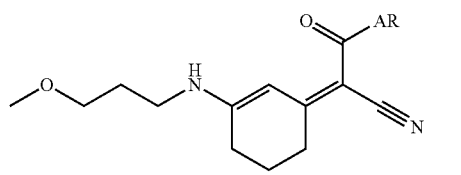

(3)

in which:
A is —O— or —NH;
R is a C1-C22 alkyl group, a C2-C22 alkenyl group, a C2-C22 alkynyl group, a C3-C22 cycloalkyl group or a C3-C22 cycloalkenyl group, said groups possibly being interrupted with one or more O;
b) at least one oily phase comprising at least one alkyl or alkylene carbonate, present in concentrations ranging from 0.1% to 98% by weight relative to the total weight of the composition.

18. The composition according to claim 1, in which the alkylene chain(s) of the alkylene carbonate(s) is (are) a C2-C6 alkyl radical;
and/or in which the alkyl radical(s) of the alkyl carbonate(s) is (are) a C1-C6 alkyl radical.

19. The composition according to claim 1, in which the sum of the carbons of the alkylene chain(s) of alkylene carbonate(s) and/or the sum of the carbons of the alkyl radical(s) of alkyl carbonate(s) is (are) ranging from 2 to 6 carbon atoms.

20. The composition according to claim 1, in which the alkylene carbonate(s) are chosen from the alkylene carbonates of formula (4) below:

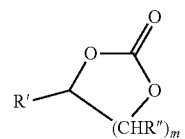

in which formula (4)
R' denotes a hydrogen atom, a linear or branched $C_1$-$C_6$ alkyl radical, a linear or branched $C_1$-$C_4$ hydroxyalkyl radical;
R" represents a hydrogen atom, a linear or branched $C_1$-$C_6$ alkyl radical, a linear or branched $C_1$-$C_4$ hydroxyalkyl radical;
m is 1, 2 or 3.

21. The composition according to claim 1, in which the alkylene carbonate(s) are chosen from the alkylene carbonates of formula (4) below:

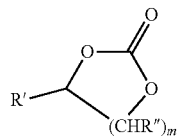

in which formula (4)
the radical R' represents a hydrogen atom, a linear or branched $C_1$-$C_4$ alkyl radical, a linear $C_1$-$C_2$ hydroxyalkyl radical;
R" represents a hydrogen atom, a linear or branched $C_1$-$C_2$ alkyl radical, a linear $C_1$-$C_2$ hydroxyalkyl radical,
and m is 1.

22. The composition according to claim 1, in which the alkylene carbonate(s) are chosen from ethylene carbonate, propylene carbonate, 1,2-butylene carbonate and glyceryl carbonate.

23. The composition according to claim 1, in which the alkyl carbonate(s) are chosen from those of formula (5) below:

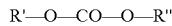

R'—O—CO—O—R"

in which formula (5)
R' denotes a linear or branched $C_1$-$C_5$ alkyl radical, a linear or branched $C_1$-$C_4$ hydroxyalkyl radical;
R" represents a linear or branched $C_1$-$C_5$ alkyl radical, a linear or branched $C_1$-$C_4$ hydroxyalkyl radical;
the sum of the carbons of R' and R" ranging from 2 to 6.

24. The composition according to claim 1, in which the alkyl carbonate(s) are chosen from diethyl carbonate and dipropyl carbonate.

25. The composition according to claim 1, in which the alkyl or alkylene carbonate(s) are present in concentrations ranging from 0.1% to 98% by weight relative to the total weight of the composition.

26. The composition according to claim 1, further comprising an additional UV-screening agent.

27. The composition according to claim 1, in which the merocyanine(s) are present in a concentration ranging from 0.1% to 25% by weight relative to the total weight of the composition, the alkyl or alkylene carbonate(s) are present in concentrations ranging from 0.1% to 98% by weight relative to the total weight of the composition and the at least one oily phase is present in a concentration ranging from 5% to 98% by weight relative to the total weight of the composition.

28. The composition according to claim 1, in which the merocyanine(s) are present in a concentration ranging from 0.2% to 20% by weight relative to the total weight of the composition, the alkyl or alkylene carbonate(s) are present in concentrations ranging from 0.5% to 50% by weight relative to the total weight of the composition and the at least one oily phase is present in a concentration ranging from 10% to 80% by weight relative to the total weight of the composition.

29. The composition according to claim 1, in which the merocyanine(s) are present in a concentration ranging from 0.5% to 10% by weight relative to the total weight of the composition, the alkyl or alkylene carbonate(s) are present in concentrations ranging from 5% to 15% by weight relative to the total weight of the composition and the at least one oily phase is present in a concentration ranging from 10% to 80% by weight relative to the total weight of the composition.

30. A non-therapeutic cosmetic process for caring for and/or making up a keratin material, comprising application, to a surface of said keratin material, of at least one composition as defined in claim 1.

31. A non-therapeutic cosmetic process for limiting darkening of skin and/or improving colour and/or uniformity of a complexion, comprising application, to a surface of the skin, of at least one composition as defined in claim 1.

32. A non-therapeutic cosmetic process for preventing and/or treating signs of ageing of a keratin material, comprising application, to a surface of the keratin material, of at least one composition as defined in claim 1.

\* \* \* \* \*